United States Patent
Florescu

(10) Patent No.: US 9,568,415 B2
(45) Date of Patent: Feb. 14, 2017

(54) MAGNETIC PARTICLE BASED BIOSENSOR

(71) Applicant: Silicon BioDevices, Inc., Palo Alto, CA (US)

(72) Inventor: Octavian Florescu, Berkeley, CA (US)

(73) Assignee: Silicon BioDevices, Inc., Palo Alto, CA (US)

( * ) Notice: Subject to any disclaimer, the term of this patent is extended or adjusted under 35 U.S.C. 154(b) by 691 days.

(21) Appl. No.: 13/858,794

(22) Filed: Apr. 8, 2013

(65) Prior Publication Data

US 2013/0230913 A1 Sep. 5, 2013

Related U.S. Application Data

(63) Continuation of application No. PCT/US2011/055467, filed on Oct. 7, 2011.
(Continued)

(51) Int. Cl.
| | |
|---|---|
| *G01N 33/553* | (2006.01) |
| *G01N 21/17* | (2006.01) |
| *G01N 21/25* | (2006.01) |
| *G01N 21/78* | (2006.01) |
| *G01N 33/543* | (2006.01) |

(Continued)

(52) U.S. Cl.
CPC ............ *G01N 21/17* (2013.01); *G01N 21/253* (2013.01); *G01N 21/78* (2013.01); *G01N 33/54326* (2013.01); *G01N 33/54366* (2013.01); *G01N 15/1436* (2013.01); *G01N 21/274* (2013.01)

(58) Field of Classification Search
None
See application file for complete search history.

(56) References Cited

U.S. PATENT DOCUMENTS 4,810,658 A * 3/1989 Shanks .................. G01N 21/03
                                                            250/227.31
6,710,878 B1    3/2004 Dean et al.
(Continued)

FOREIGN PATENT DOCUMENTS

WO    WO 2009/091926    7/2009
WO    WO 2011/045570    4/2011
(Continued)

OTHER PUBLICATIONS

Dupont, Emile P. et al., "Fluorescent magnetic bead and cell differentiation/counting using a CMOS SPAD matrix," Sensors and Actuators B: Chemical, vol. 174, Nov. 1, 2012, pp. 609-615, XP55113691, ISSN: 0925-4005, DOI: 10.1016/j.snb.2012.06.049.
Dupont, Emile P. et al., "Monolithic Silicon Chip for Immunofluorescence Detection on Single Magnetic Beads," Analytical Chemistry, vo 1. 82, No. 1, Jan. 1, 2010, pp. 49-52, XP55113678, ISSN: 0003-2700, DOI: 10.1021/ac902241j.
(Continued)

*Primary Examiner* — Chris L Chin
(74) *Attorney, Agent, or Firm* — Levine Bagade Han LLP

(57) ABSTRACT

A biosensor system and method of its use for detecting particles on the surface of an integrated circuit is disclosed. The system can include a light source and a plurality of optical sensors formed on an integrate circuit. The particles can be positioned the surface of the integrated circuit whereby the particles can cast a shadow or shadows that reduces the amount of light transmitted from the light source to the optical sensors. The surface of the integrated circuit can include one or more optical sensing areas whereby the presence of one or more particles may significantly or measurably reduce the amount of light incident on one or more optical sensor.

17 Claims, 30 Drawing Sheets

Related U.S. Application Data

(60) Provisional application No. 61/390,809, filed on Oct. 7, 2010, provisional application No. 61/415,183, filed on Nov. 18, 2010.

(51) Int. Cl.
  *G01N 15/14* (2006.01)
  *G01N 21/27* (2006.01)

(56) References Cited

U.S. PATENT DOCUMENTS

| | | | |
|---|---|---|---|
| 7,736,890 | B2 | 6/2010 | Sia et al. |
| 8,217,436 | B2 * | 7/2012 | Henderson ............ H01L 31/107 257/292 |
| 2002/0197456 | A1 | 12/2002 | Pope |
| 2005/0244953 | A1 | 11/2005 | Cohen |
| 2006/0084069 | A1 * | 4/2006 | Chan ................. G01N 21/6428 435/6.15 |
| 2006/0246601 | A1 | 11/2006 | Song et al. |
| 2008/0180673 | A1 | 7/2008 | Sampas et al. |
| 2008/0186494 | A1 | 8/2008 | Kiesel et al. |
| 2009/0121147 | A1 | 5/2009 | Kahlman |
| 2012/0046203 | A1 * | 2/2012 | Walsh .................... A61B 5/157 506/39 |

FOREIGN PATENT DOCUMENTS

| | | |
|---|---|---|
| WO | WO 2011/059512 | 5/2011 |
| WO | WO 2012/048288 | 4/2012 |

OTHER PUBLICATIONS

Gijs, et al., "Microfluidic applications of magnetic particles for biological analysis and catalysis," Chemical Reviews, American Chemical Society, US, vol. 110, No. 3, Jan. 1, 2010, pp. 1518-1563, XP007917138, ISSN: 0009-2665. DOI: 10.1021/CR9001929 [retrieved on Apr. 12, 2009].

Lehmann et al., "Actuation and detection of magnetic microparticles in a bioanalytical microsystem with integrated CMOS chip," Jan. 1, 2009, Nanosystems Design and Technology, Springer, NL, pp. 85-102, XP009177574, ISBN: 978-1-4419-0255-9.

Lehmann, U. et al., "A CMOS Microsystem Combining Magnetic Actuation and In-Situ Optical Detection of Microparticles," Solid-State Sensors, Actuators and Microsystems Conference, 2007. Transducers 2007. International, IEEE, Piscataway, NJ, USA, Jun. 10, 2007, pp. 2493-2496, XP031216577, ISBN: 978-1-4244-0841-2.

Lehmann, U. et al., "Microparticle photometry in a CMOS microsystem combining magnetic actuation and in situ optical detection," Sensors and Actuators B: Chemical International Journal Devoted to Research and Development of Physical and Chemical Transducers, Elsevier S.A, CH, vol. 132, No. 2, Jun. 16, 2008, pp. 411-417, P022707530, ISSN: 0925-4005, DOI: 10.1016/J.SNB.2007.10.021, [retrieved on Oct. 23, 2007].

Lehmann, Ulrike et al., "Particle Shadow Tracking—Combining Magnetic Particle Manipulation with In-Situ Optical Detection in a CMOS Microsystem," Jul. 16, 2007, XP55113527, Retrieved from the Internet: URL:http://infoscience.epfl.ch/record/113845, [retrieved on Apr. 10, 2014].

\* cited by examiner

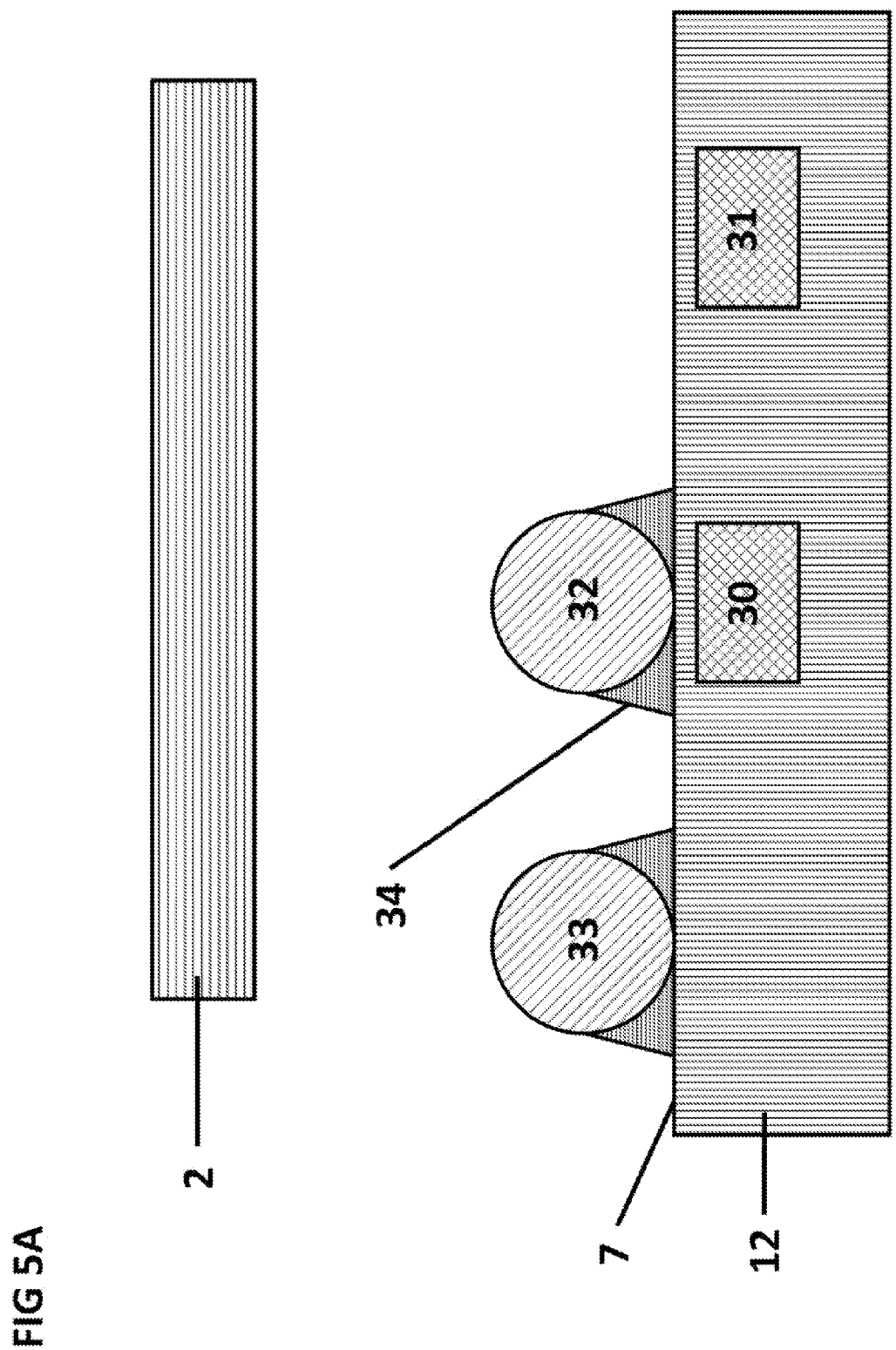

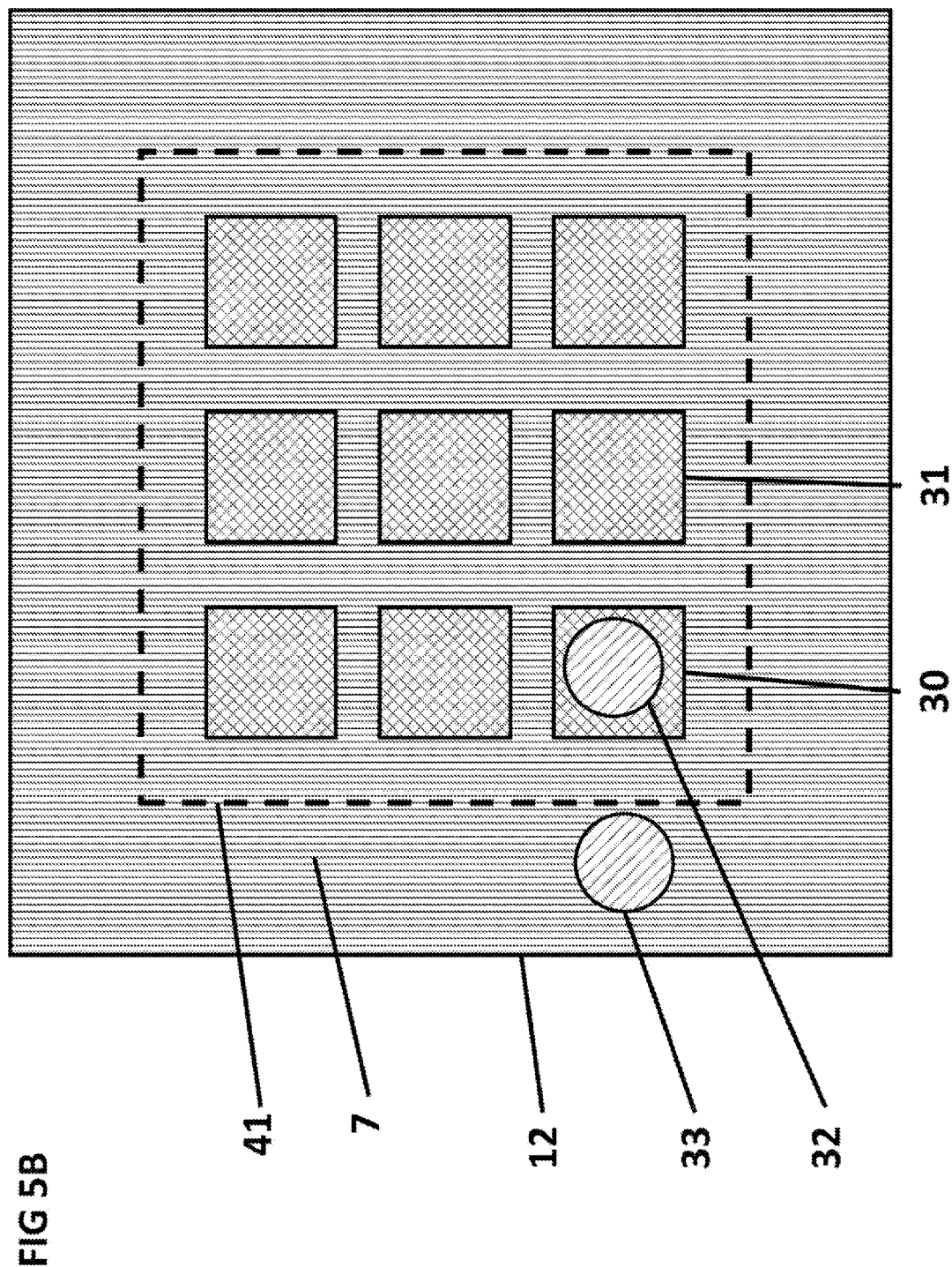

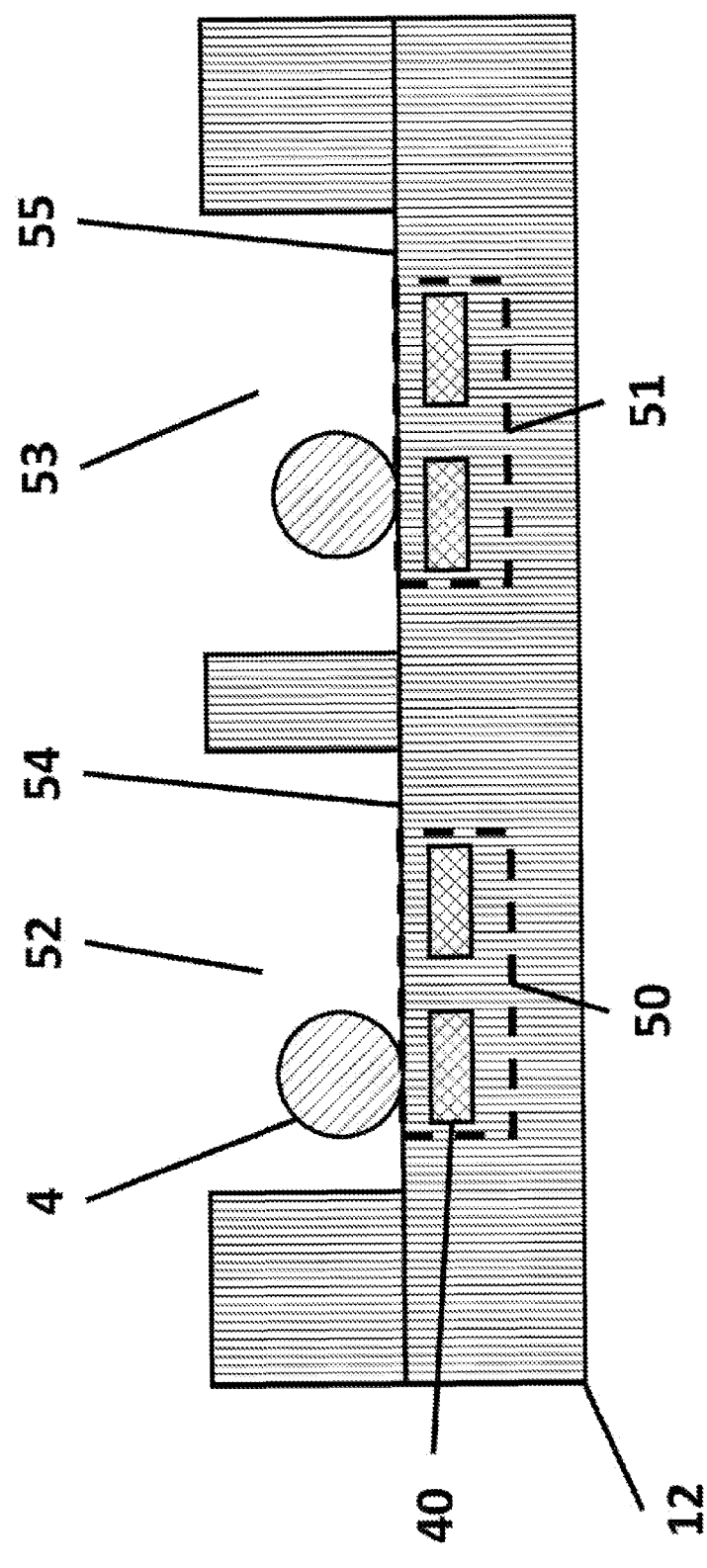

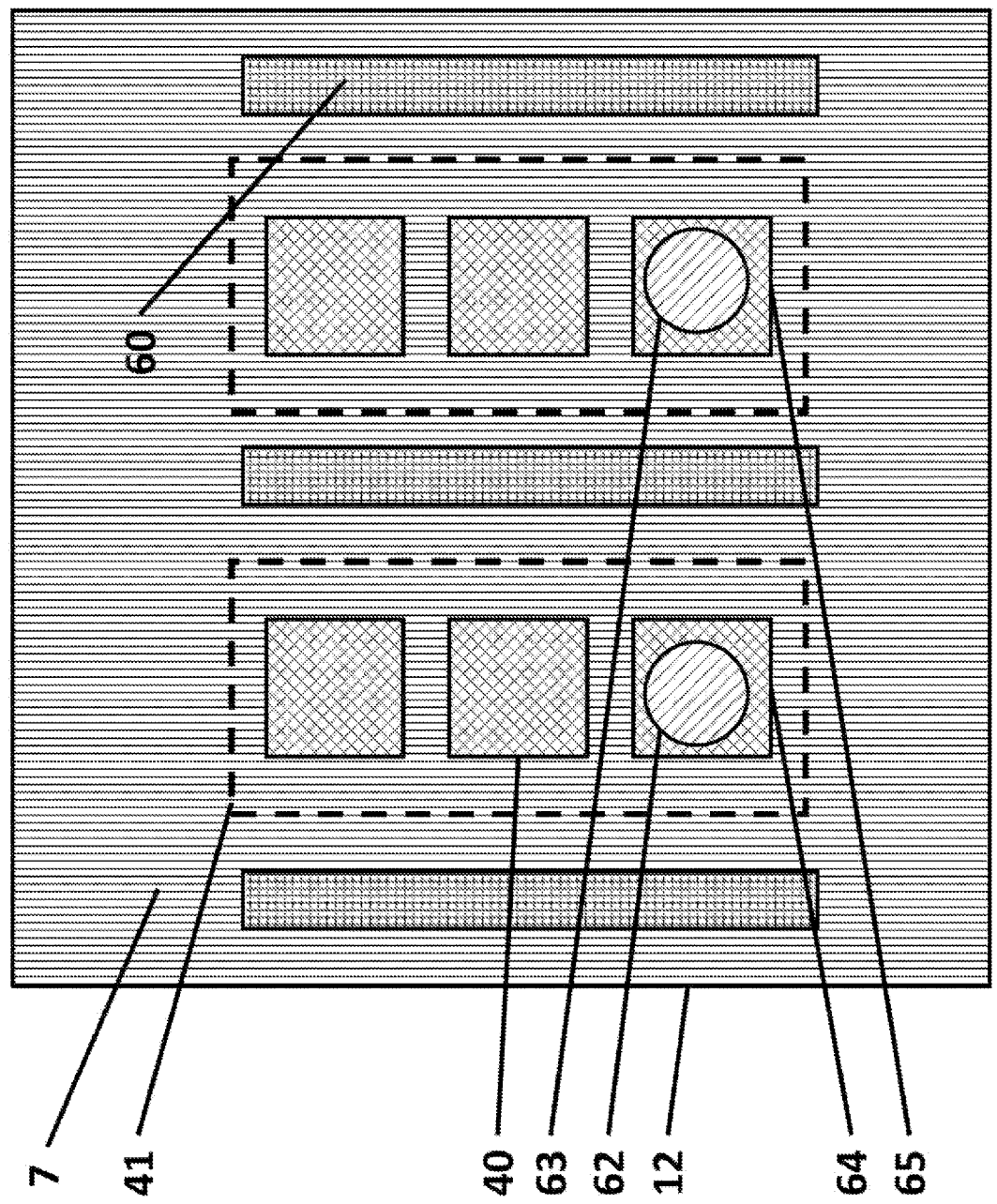

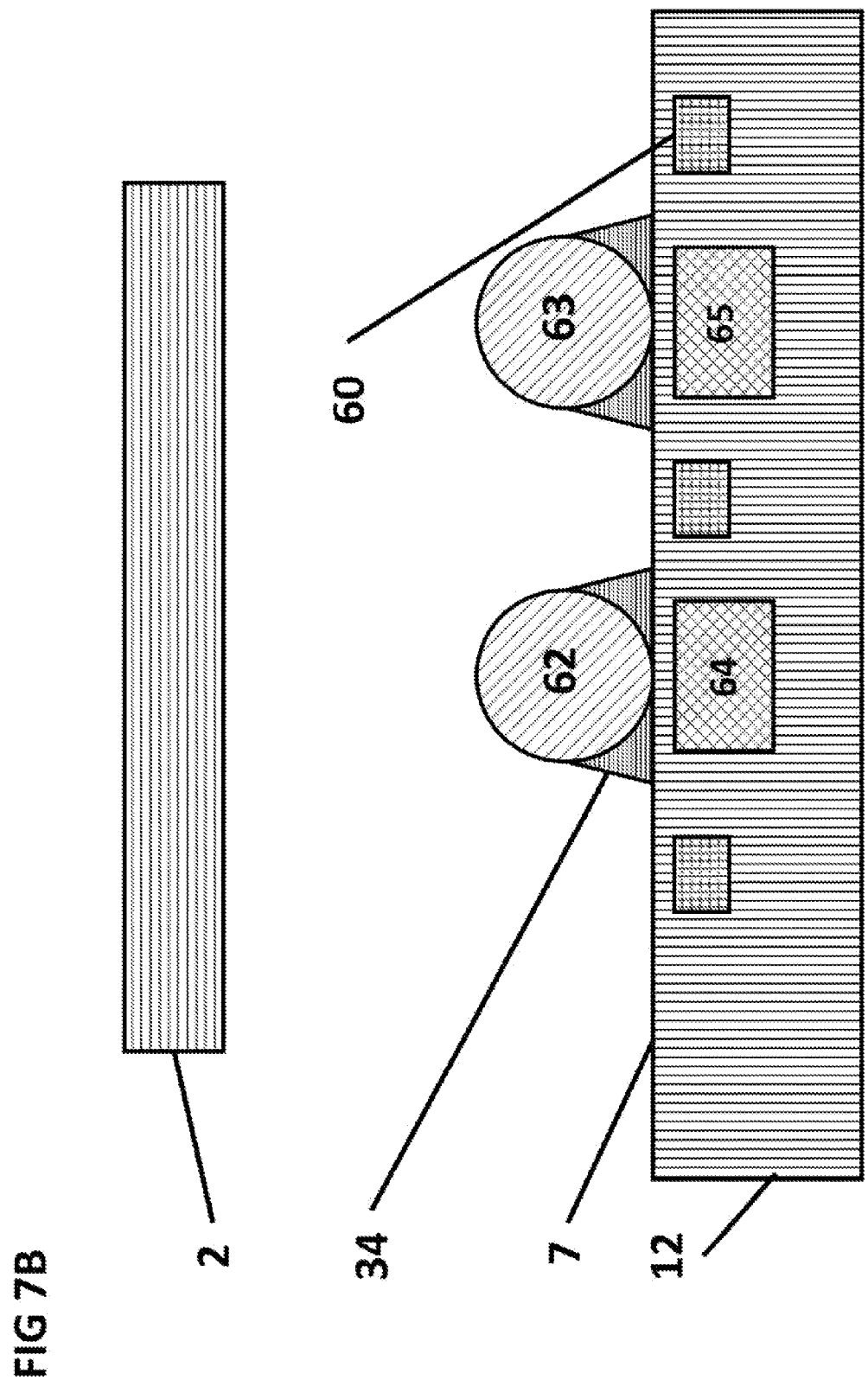

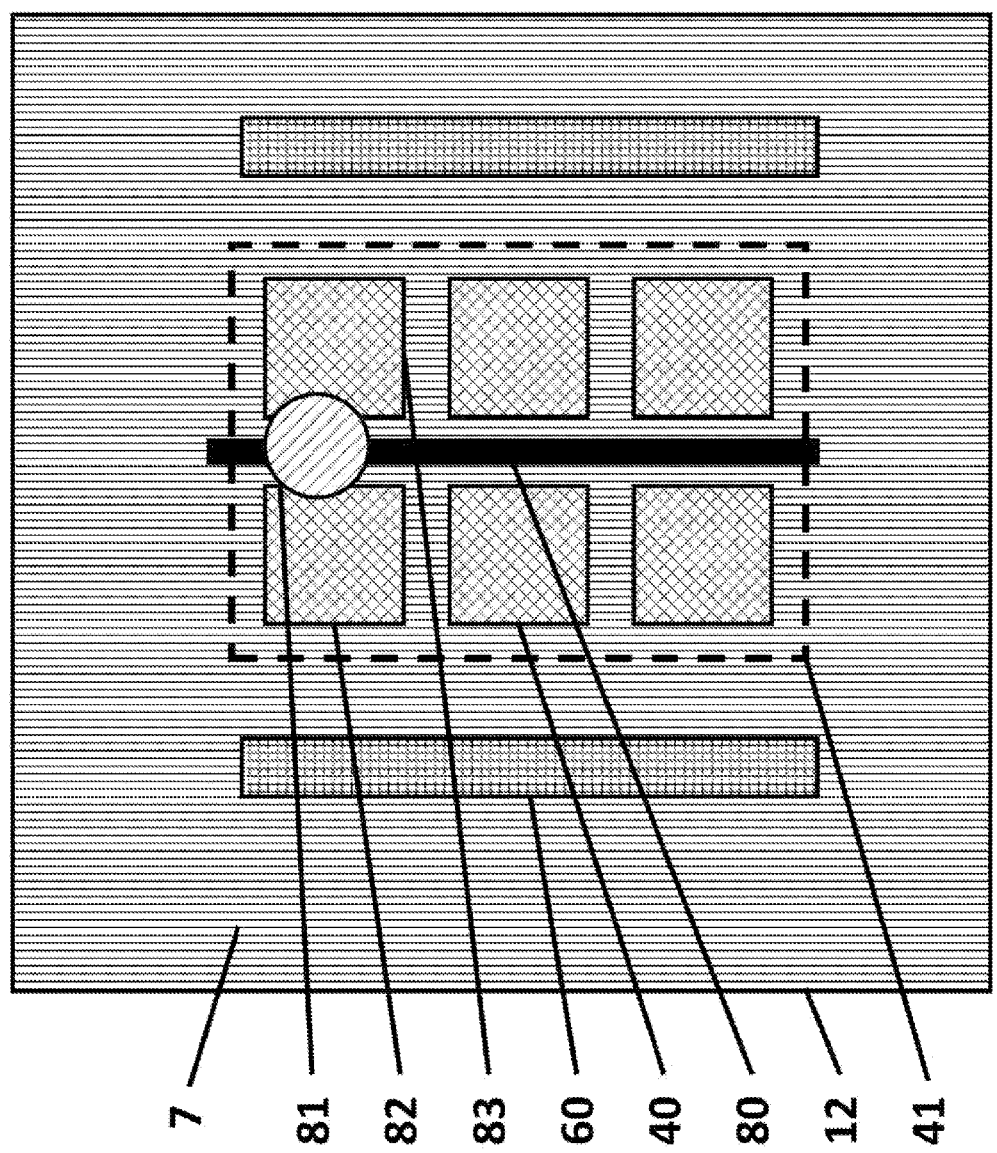

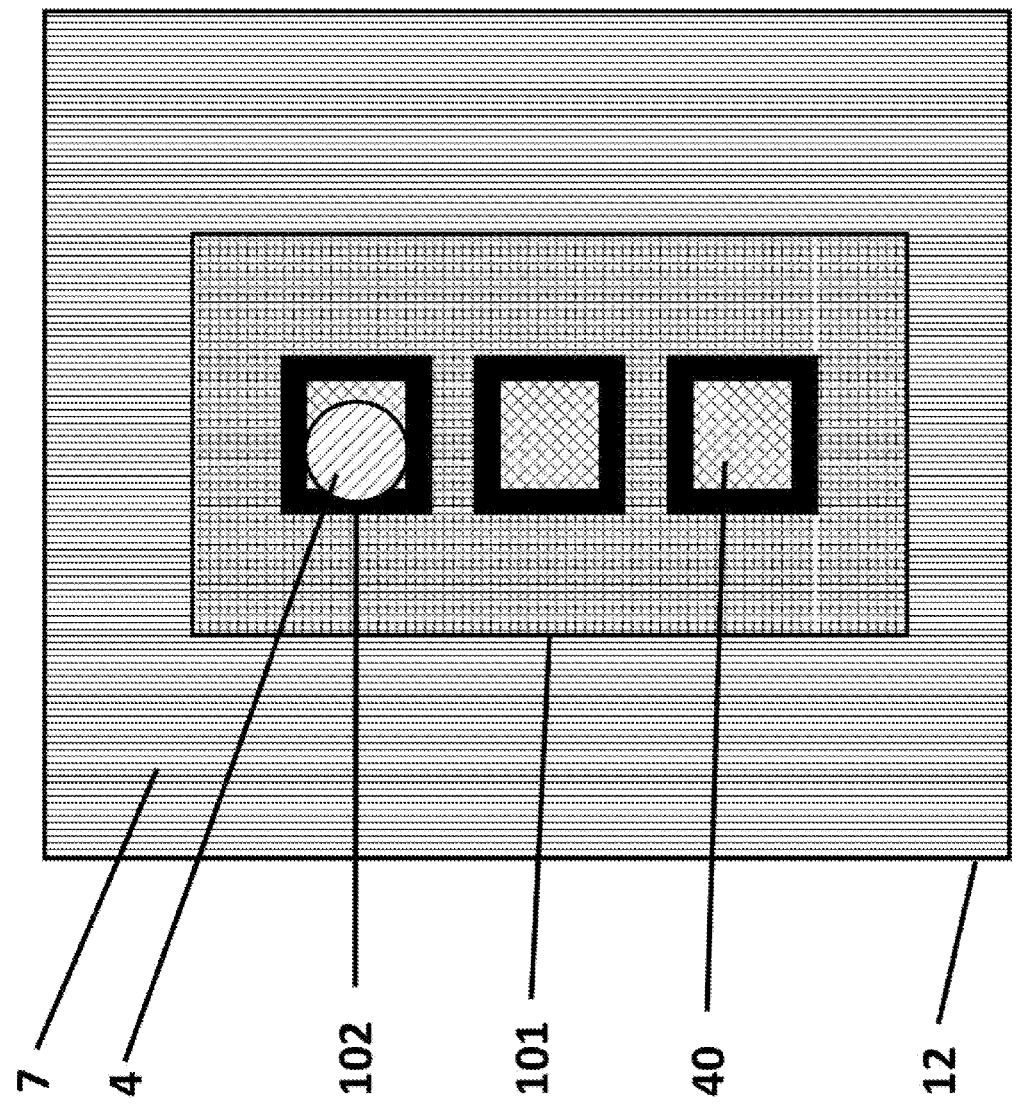

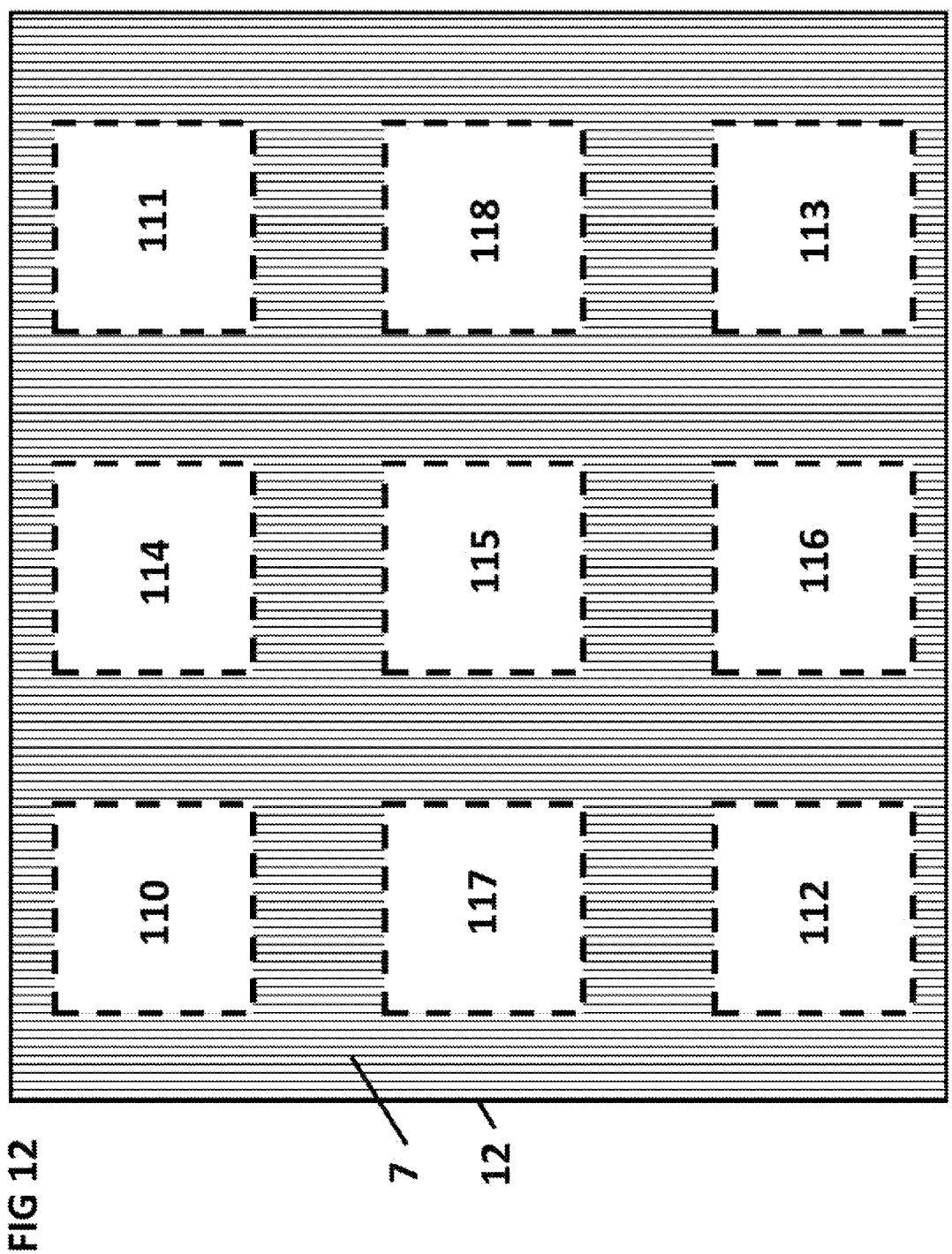

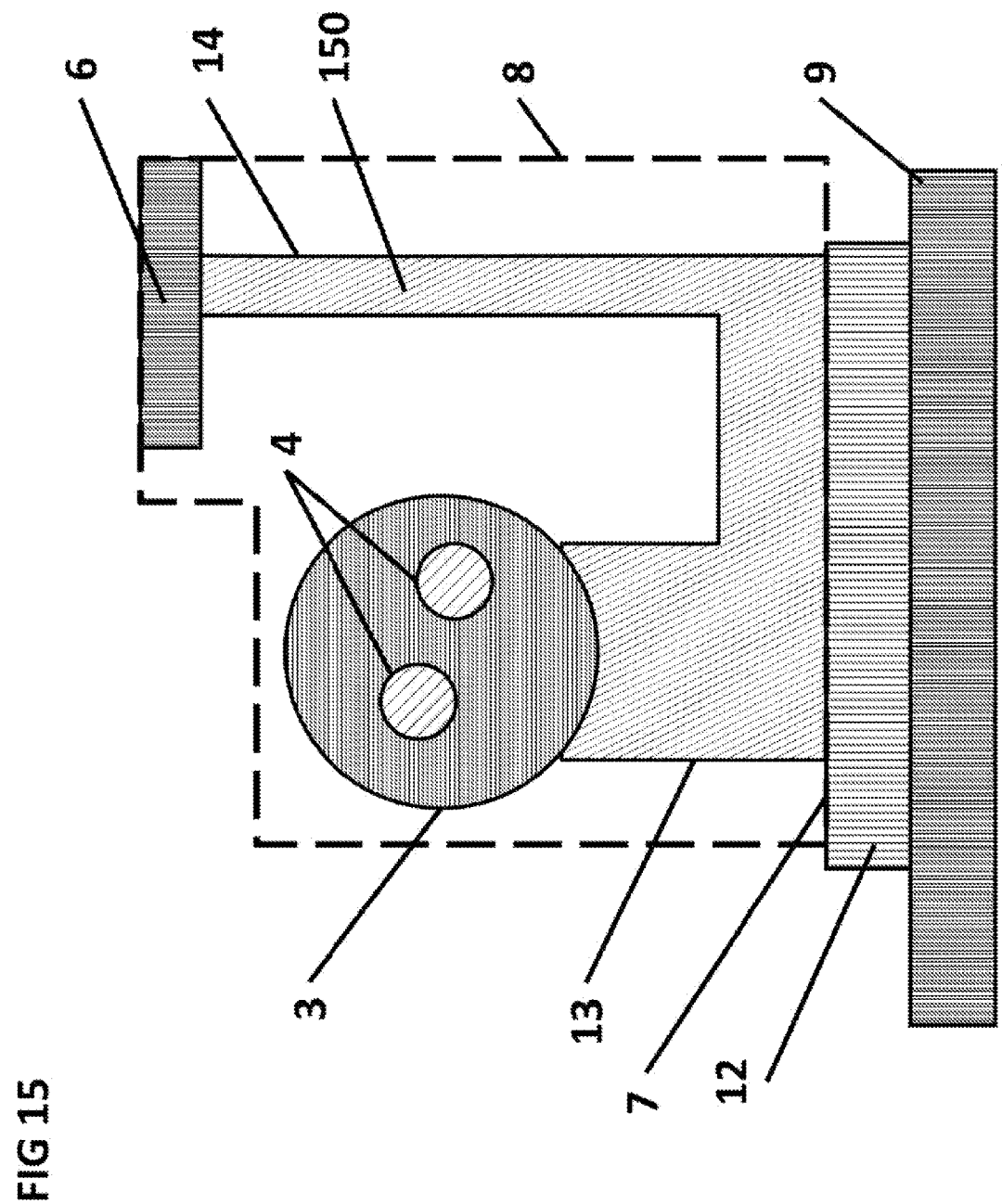

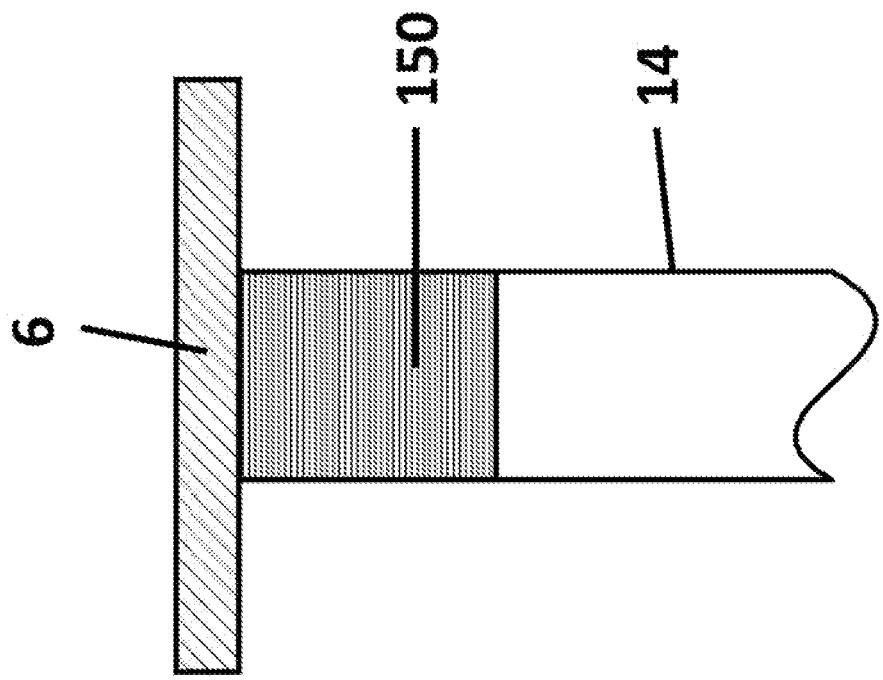
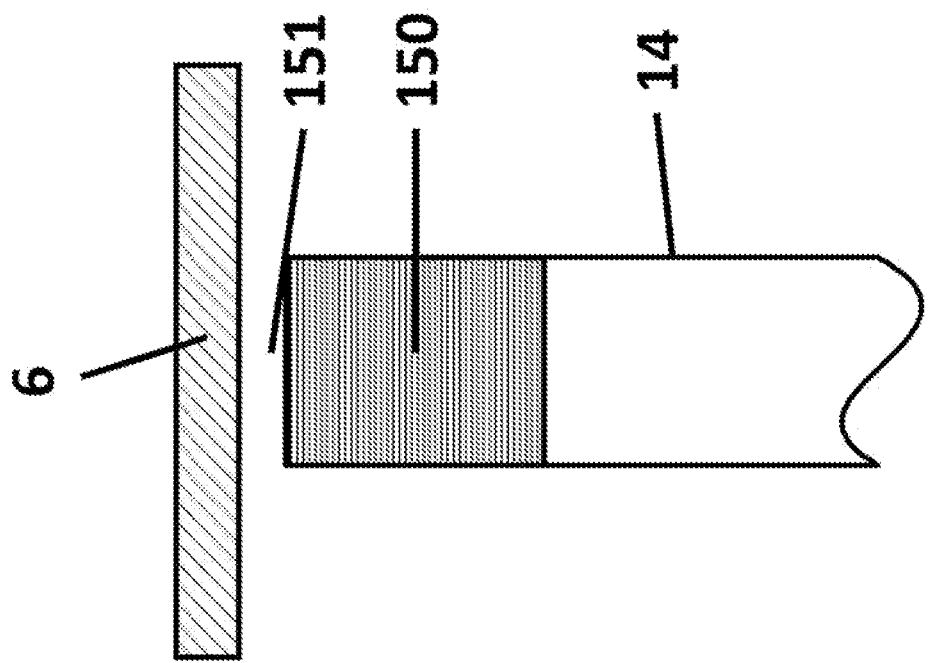

MAGNETIC PARTICLE BASED BIOSENSOR

CROSS-REFERENCE TO RELATED APPLICATIONS

This application is a continuation of PCT Application No. US2011/055467, filed 7 Oct. 2011, which claims priority to U.S. Provisional Application Nos. 61/390,809, filed 7 Oct. 2010, and 61/415,183, filed 18 Nov. 2010, all of which are incorporated by reference herein in their entireties.

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

SUMMARY OF THE INVENTION

Systems, devices and methods for detecting and manipulating magnetic particles are disclosed. Various aspects of the variations described herein may be applied to any of the particular applications set forth below or for any other types of sensors. The variations disclosed may be applied as a standalone system or method, or as part of integrated detection or biosensor systems. Different aspects of the variations disclosed can be used individually, collectively, or in combination with each other.

A biosensor configured to detect magnetic particles is disclosed. The system can have a light source and an integrated circuit containing optical sensors. Particles on the surface of the integrated circuit can cast a shadow that can change the amount of light from the light source that is received by the optical sensors. In this way the particles generate a contrast ratio, defined as the ratio of light detected by an optical sensor with no particle positioned over said optical sensor divided by the light detected by the optical sensor with a particle positioned over said optical sensor. The optical sensors can detect the magnetic particles by measuring the amount of incident light on an optical sensing area. The optical sensing area may be described as the area on the surface of the integrated circuit containing one or more optical sensors capable of detecting particles. One or more distinct optical sensing areas can be on the surface of the integrated circuit.

The system, for example in a biosensing format, can detect magnetic particles 81 that can bind strongly and/or specifically to the surface of the integrated circuit as a result of one or more chemical reactions involving one or more target species in an aqueous sample.

The magnetic particles can react with one or more target species in aqueous sample. The magnetic particles can be attracted to the optical sensing area on the biologically coated surface of the integrated circuit by magnetic concentration forces that can be generated by current passing through concentration conductors embedded in the integrated circuit. The magnetic particles that react with the target species can bind specifically to the surface of the integrated circuit exposed to the aqueous sample. The magnetic particles that do not react with the target species can bind non-specifically to the surface of the integrated circuit and can be removed from the optical sensing area.

One or more magnetic separation field generators embedded in the integrated circuit can produce magnetic separation forces. The magnetic separation forces can remove the non-specifically bound magnetic particles from the optical sensing area, for example such that only the specifically bound magnetic particles remain.

The magnetic particles remaining in the optical sensing area can cast a shadow and reduce the amount light transmitted from the light source to the optical sensors. The optical sensors can detect the presence of the magnetic particles by measuring the amount of incident light.

The optical sensors can be similar in size to the magnetic particle such that each sensor can only detect the presence of one particle.

The optical sensors can be individually addressable and her electrical signals can be amplified, digitized, stored and processed by circuitry internal or external to the integrated circuit.

The details of these and other variations are set forth in the accompanying drawings and the description below.

BRIEF DESCRIPTION OF THE DRAWINGS

FIGS. 5A and 5B are cross sectional side and top views, respectively, of a variation of the IC 12 with two optical sensors 40 and two particles on its surface 7 casting shadows. Particle 32 can be detected by the optical sensor 30, while optical sensor 31 cannot detect any particles.

FIG. 6 is a cross sectional side view of trenches etched into the IC.

FIGS. 7A and 7B are top and cross sectional side views, respectively, of a variation of the IC 12 containing a magnetic separation field generator implemented with separation conductors.

FIGS. 9A and 9B are top and cross sectional side views, respectively, of a variation of the IC 12 that can have a separation conductor 60 and a concentration conductor 80.

FIGS. 11A and 11B are top and cross sectional side views, respectively, of a variation of the IC 12 with light shield layers 101.

FIG. 12 is a top view of a variation of the IC 12 with a surface 7 that has been coated with multiple reagents and controls.

FIG. 15 is a cross sectional side view of a variation of the system 10 with dried reagent 150 throughout the delivery capillary 14 and the sedimentation capillary 13 that can promote wicking of the aqueous sample 5.

FIGS. 16A and 16B are cross sectional side views of a variation of the inlet to the delivery capillary 14.

DETAILED DESCRIPTION

Biosensors that use non-magnetic or magnetic particle labeling to perform assays are disclosed. A label particle serves as an aid in detecting the presence of specific binding between a receptor and the target analyte which may consist of immunological bonds, nucleic acid bonds, covalent bonds, ionic bonds, hydrogen bonds, and other binding phenomena capable of being differentiated from non-specific binding).

Particles may be any spherical or arbitrarily shaped localized objects, from several nanometers to tens of microns in diameter, that modulate incoming light (e.g., reflect the light, refract the light, block the light, increase the intensity of the light, change the wavelength or spectral composition of the light). Magnetic panicles also display diamagnetic, ferromagnetic, ferrimagnetic, paramagnetic, superparamagnetic, or antiferromagnetic behavior. Magnetic particles may include individual nanometer-sized particles of magnetic material (often referred to as magnetic nanoparticles or magnetizable nanoparticles) or larger aggregates of such magnetic nanoparticles to form an essentially spherical bead (often referred to as magnetic beads, magnetizable beads). Magnetic particles may be covered with or encapsulated by a non-magnetic material, such as a polymer, ceramic, or any other non-magnetic material, that may be coated with biological or chemical molecules to react specifically to a target analyte. A non-magnetic material refers to any material that displays no magnetic properties or displays magnetic properties that are much smaller in magnitude (e.g., less than 1%) than the magnetic material in magnetic particles. Magnetic particles may be from several nanometers to tens of microns in diameter.

Figure 1:
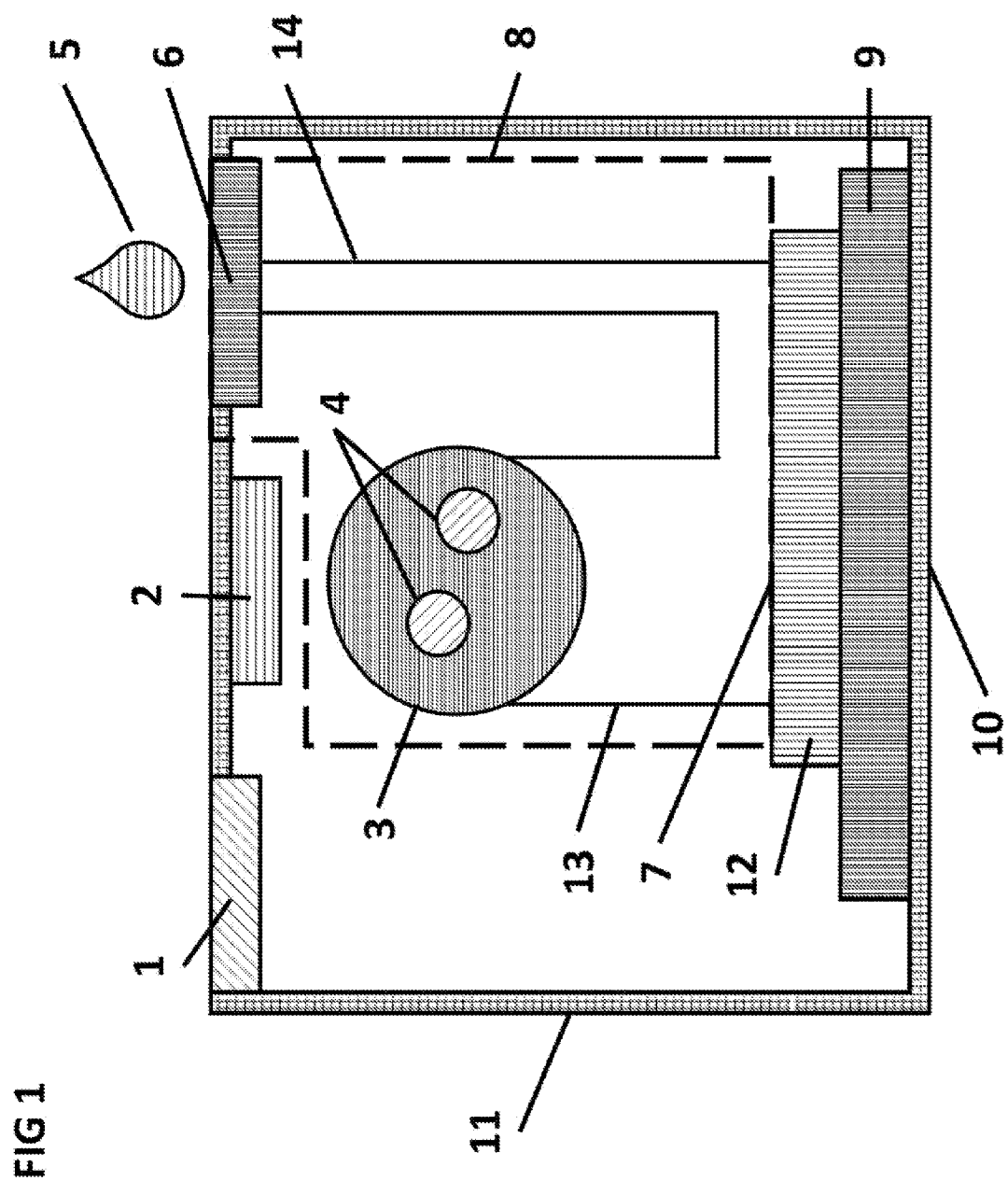
FIG. 1 is a cross sectional side view of a variation of the system 10 that includes a sample preparation and delivery module (SPDM) 8, a light source 2, an integrated circuit 12 (IC), a printed circuit hoard (PCB) 9, a display 1, and a casing 11.

FIG. 1 shows a system 10 that includes a sample preparation and delivery module (SPDM) 8, a light source 2, an integrated circuit (IC) 12, a printed circuit board (PCB) 9, a display 1, and a casing 11. The system 10 may be configured to perform a biological and/or chemical assay on an aqueous sample 5 by introducing, detecting, and/or quantifying particles 4 binding on the surface 7 of the IC 12. An assay may be any procedure used to detect the presence of a target analyte or to quantify the concentration or amount of the target analyte in the aqueous sample 5. Target analytes may be enzymes, proteins, small molecules, nucleic acids, and other biological, chemical, and inorganic species, or combinations thereof. The aqueous sample 5 may be whole blood, plasma, serum, diluted blood derivatives, sputum, pulmonary lavage, fecal samples, oral samples, nasal samples, lachrymal fluid, other bodily fluids, laboratory samples, environmental samples, any other fluids potentially containing one or more target analytes, or combinations thereof. The systems and methods of their use as described herein can be applied to known target analyte detection schemes such as those described in PCT Publication No. WO 2009/091926, filed 15 Jan. 2009 (titled: INTEGRATED MAGNETIC 12FIELD GENERATION AND DETECTION PLATFORM) which is incorporated by reference herein in its entirety. Any one of the components described above may be omitted, replaced, or modified.

Further, FIG. 1 shows a filter 6 that can be placed at the top of the SPDM 8. The filter 6 may be any type of titter (e.g., membrane filter, microfilter, syringe filter) capable of blocking or trapping particulate matter (e.g., red blood cells, white blood cells, other cells and micron to millimeter size particulates) and thus removing the particulate matter from the aqueous sample 5. The filter 6 may also be adapted to remove certain biological or chemical molecules from the aqueous sample 5 (e.g., a chemical coating on the filter 6 may remove molecules that compete with the target analyte or interfere, in any way, with the assay). Further, the filter 6 may include chemicals, molecules, and other dissolvable matter than may aid the assay protocol. For example, the filter 6 may contain anticoagulation factors that prevent blood samples from coagulating. Further still, the filter 6 may be coated in hydrophilic material to aid in aqueous sample 5 absorption.

Further, FIG. 1 shows a delivery capillary 14 and a sedimentation capillary 13. The delivery capillary 14 can connect the membrane filter 6 to the sedimentation capillary 13 and thus allow the aqueous sample 5 to flow from the filter 6 to the sedimentation capillary 13. In one variation of the system 10, the filter 6 may be placed inside the delivery capillary 14. The sedimentation capillary 13 may be placed over the IC 12 and in contact with reagents containing particles 4. The reagents may be configured in a sphere (i.e., a reagent sphere 3) or any other shape. The reagent sphere 3 may rest on top of the sedimentation capillary 13 and may preferably be dry or lyophilized. The IC 12 may be mounted by any known method (e.g., wire-bonding, flip-chip assembly, conductive epoxy, and combination thereof) to a PCB 9.

The system 10 can be encapsulated by a casing 11 with an opening for a digital display 1.

The SPDM 8 can be configured to accept an aqueous sample 5 from a sample source (e.g., a finger stick, a pipette, a syringe, or combinations thereof), filter the aqueous sample 5 using the filter 6, deliver the aqueous sample 5 to the surface 7 of the IC 12 and to the reagent sphere 3, re-hydrate dried particles 4 within the SPDM 8, mix and incubate the particles 4 with the aqueous sample 5 and subsequently introduce the particles 4 onto the surface 7 of the IC. The systems and methods of use described herein can be applied to known SPDM's such as those described in PCT Application No. WO 2011/059512, filed 16 Nov. 2010 (titled: FILTRATION DEVICE FOR ASSAYS), which is incorporated by reference herein in its entirety. Other variations, components, and functions of the SPDM 8 are further described below.

Figure 2:
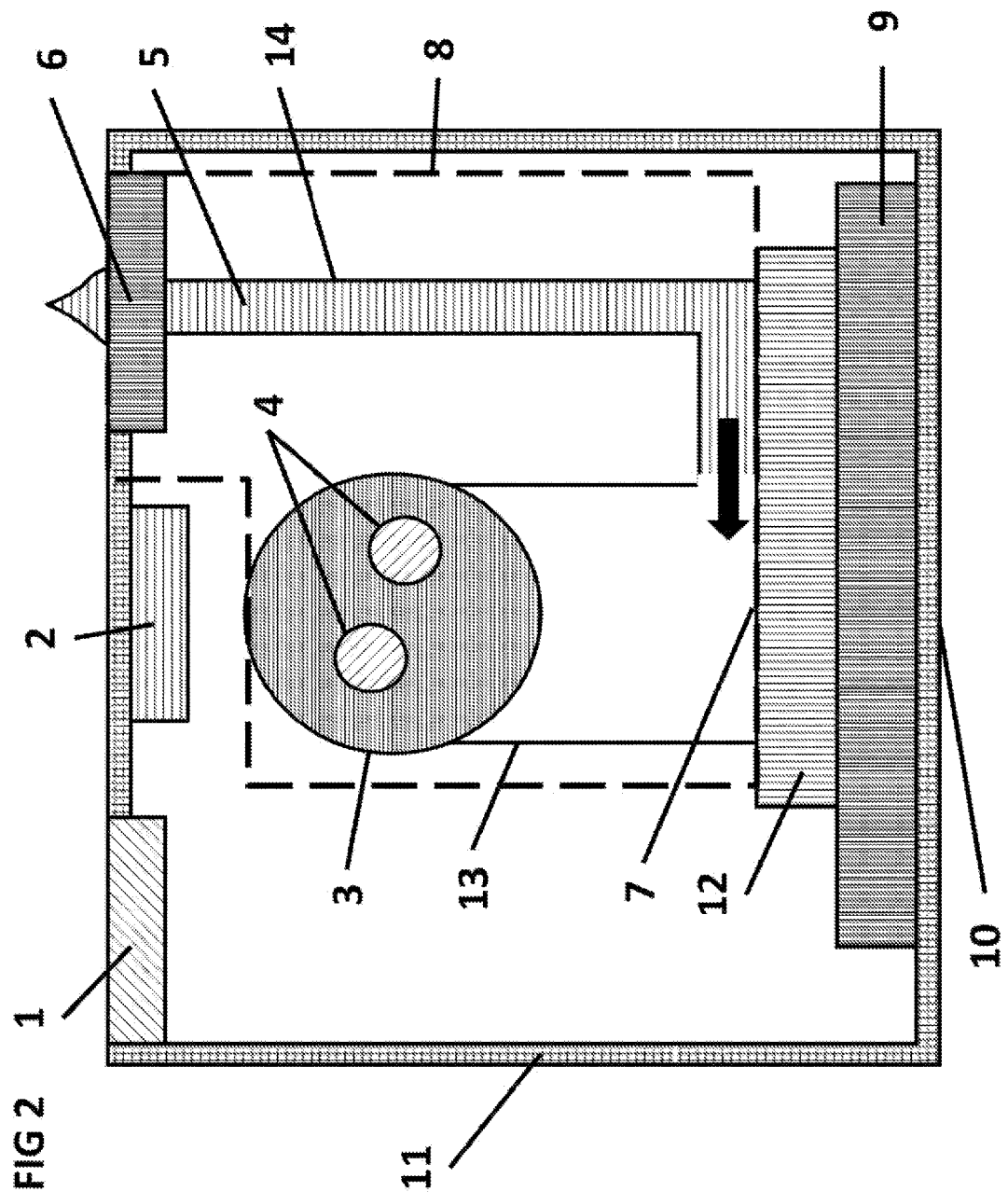
FIG. 2 is a cross sectional side view of a variation of the system 10 as the aqueous sample 5 is filtered and wicked via capillary action through a delivery capillary 14 onto a surface 7 of the integrated circuit 12.

FIG. 2 shows the aqueous sample 5 being wicked into the filter 6 where particulate matter such as whole blood cells can be blocked. The aqueous sample 5 can then be wicked from the back of the filter 6 into the delivery capillary 14 and delivered onto the surface 7 of the integrated circuit 12, as shown by an arrow. The flow in the delivery capillary 14 can be maintained by capillary action. In cases where the system 10 is placed vertically and the delivery capillary 14 is below the filter 6, gravity can also assist the flow of the aqueous sample 5. Pressure from vacuum or pumping can also be used to facilitate the flow of the aqueous sample 5 through the delivery capillary 14. As discussed above, the filter 6 may be a membrane filter and may have a surface area between 0.1 mm$^2$ and 100 cm$^2$ and a thickness between 10 μm and 2 mm. The membrane filter can be composed of polyvinylpyrrolidone/polyethersulfone (PVP/PES). The membrane filter can have a porosity gradient to effectively trap cells in whole blood while allowing blood plasma and the analytes therein to pass through the membrane. A preferable filter is a 0.26 mm thick PVP/PES filter with a 35 μm pore size on the top and a 2.5 μm pore size on the bottom. The membrane filter can be oriented in a horizontal plane. The membrane filter can be oriented in a plane parallel to the surface 7 of the IC 12. The delivery capillary 14 can be between 0.5 mm and 10 cm in length and 10 μm and 5 mm wide. A preferable delivery capillary 14 is 5 mm long and 0.25 mm wide.

Figure 3:
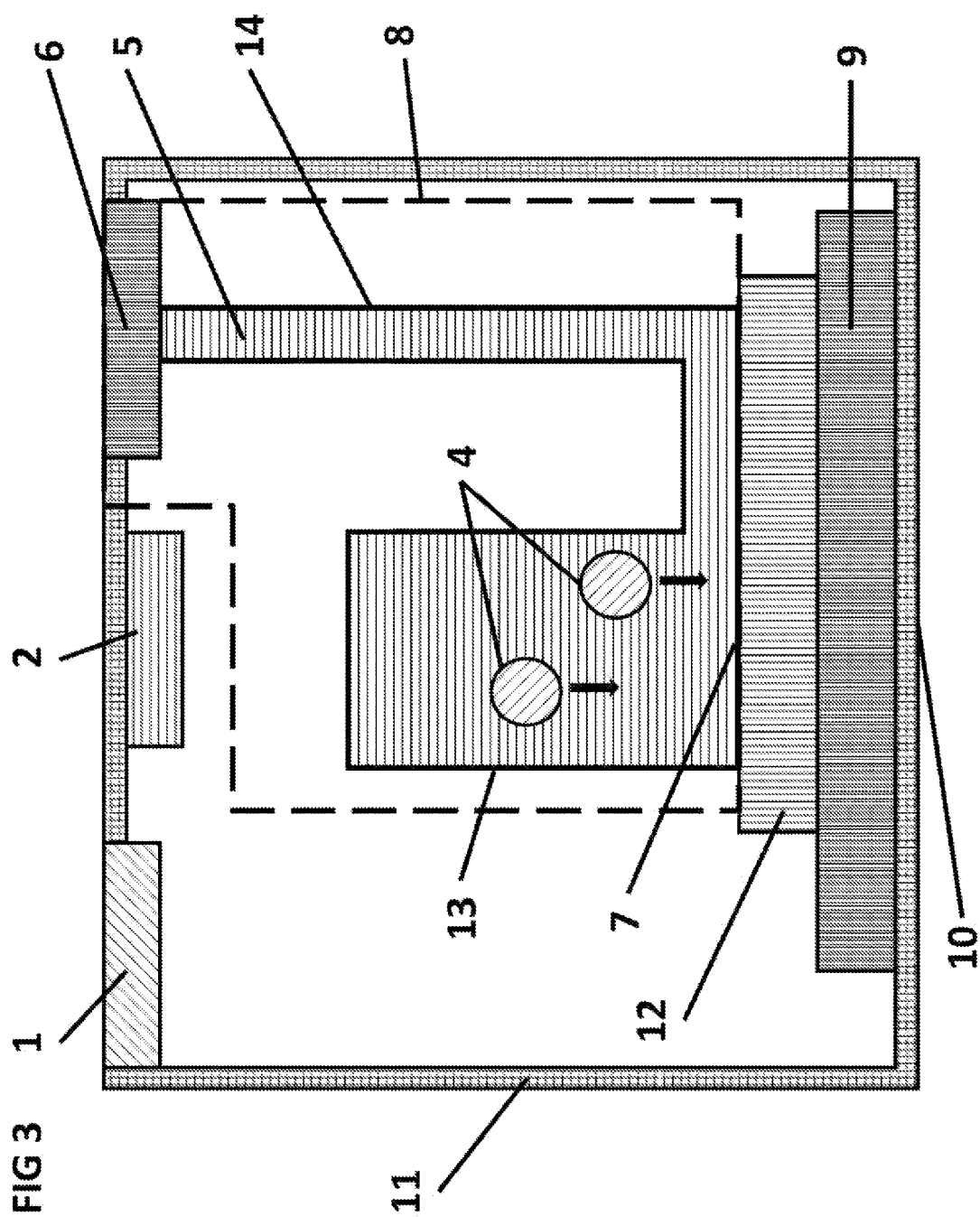
FIG. 3 is a cross sectional side view of a variation of the system 10 showing the aqueous sample 5 in the process of wicking up to sedimentation capillary 13 due to capillary action. Once the aqueous sample 5 reaches the top of the sedimentation capillary 13, the aqueous sample 5 can rehydrate a reagent sphere 3, releasing the particles 4 to sediment onto the surface 7 of the IC 12.

FIG. 3 shows the aqueous sample 5 in the process of wicking up the sedimentation capillary 13 due to capillary forces. Gravity can also assist the flow of the aqueous sample 5 up the sedimentation capillary 13 if the sedimentation capillary 13 is placed below the bottom of the filter 6. Pressure from vacuum or pumping can also be used to facilitate the flow. Once the aqueous sample 5 reaches the top of the sedimentation capillary 13, the aqueous sample 5 can rehydrate the dry reagent sphere 3 placed at the top of the sedimentation capillary 13. The particles 4 can be released and sediment through the aqueous sample 5 to the surface 7 of the integrated circuit 12, as shown by arrows. As the particles 4 sediment, the particles 4 can react with the target analytes in the aqueous sample 5 and bind specifically to the surface 7 of the IC 12. If the particles 4 do not react with any of the target analytes in the sample, the particles 4 may bind non-specifically to the surface 7 of the IC 12. The sedimentation capillary 13 can be between 0.5 mm and 10 cm in length and 10 μm and 5 mm wide. A preferable delivery capillary 14 is 3 mm long and 1 mm wide. The dry reagent sphere 3 can be manufactured by lyophilization and placed on the top of the sedimentation capillary 13 using an automated pick and place tool.

The surface 7 of the IC 12 can be illuminated by a light source 2. The light source 2 can generate and/or direct light to illuminate the surface 7 of the IC 12. The light source 2 may be or include a luminescent light source such as a LED, incandescent light source such as a light bulb, any other source of light internal or external to the system 10, or combinations thereof. The light source 2 may be any external light source (e.g., the sun, an external lamp, ambient light in a room, and any other external light source that may be used instead of or in combination with an internal light source to illuminate the surface 7 of the IC). The light source 2 may be positioned anywhere in the system 10 or external light may be inputted anywhere into the system 10 and an optical module (not shown) may direct the light onto the surface 7 of the IC 12. The light source 2 may be integrated on the IC 12 itself. For example, a direct semiconductor may be used to fabricate the IC 12 or a portion of a direct semiconductor may be added to the IC 12 (e.g., via wafer bonding, molecular beam epitaxy, and other suitable fabrication processes). The light source 2 may be configured to produce a light intensity anywhere from 1 mW/m$^2$ to 10 kW/m$^2$.

A shadow may refer to any type of light modulation caused by a particle 4 in the direction of propagation of light that increases or decreases intensity, changes the spectral composition, blocks, changes the polarization, or otherwise modifies the properties of said light. One or more light sources can be situated or positioned directly above the integrated circuit 12 such that particles 4 situated above the surface 7 of the IC 12 cast a shadow that is protected downward onto the surface 7 of the IC. The shadow then may be detected by one or more optical sensors 40 situated below the surface 7 of the IC 12. However, the light source(s) may be positioned and directed at any angle relative to the surface 7 of the integrated circuit 12 such that the light shines on least a portion of IC 12 surface 7.

In a variation of the system 10, multiple sources of light may illuminate the surface 7 of the IC 12 indirectly and/or at oblique angles. Multiple ICs can be illuminated by one source of light. The shadows or otherwise the modulated light due to the particles 4 can be projected at oblique angles (i.e., not straight downward).

Figure 4:
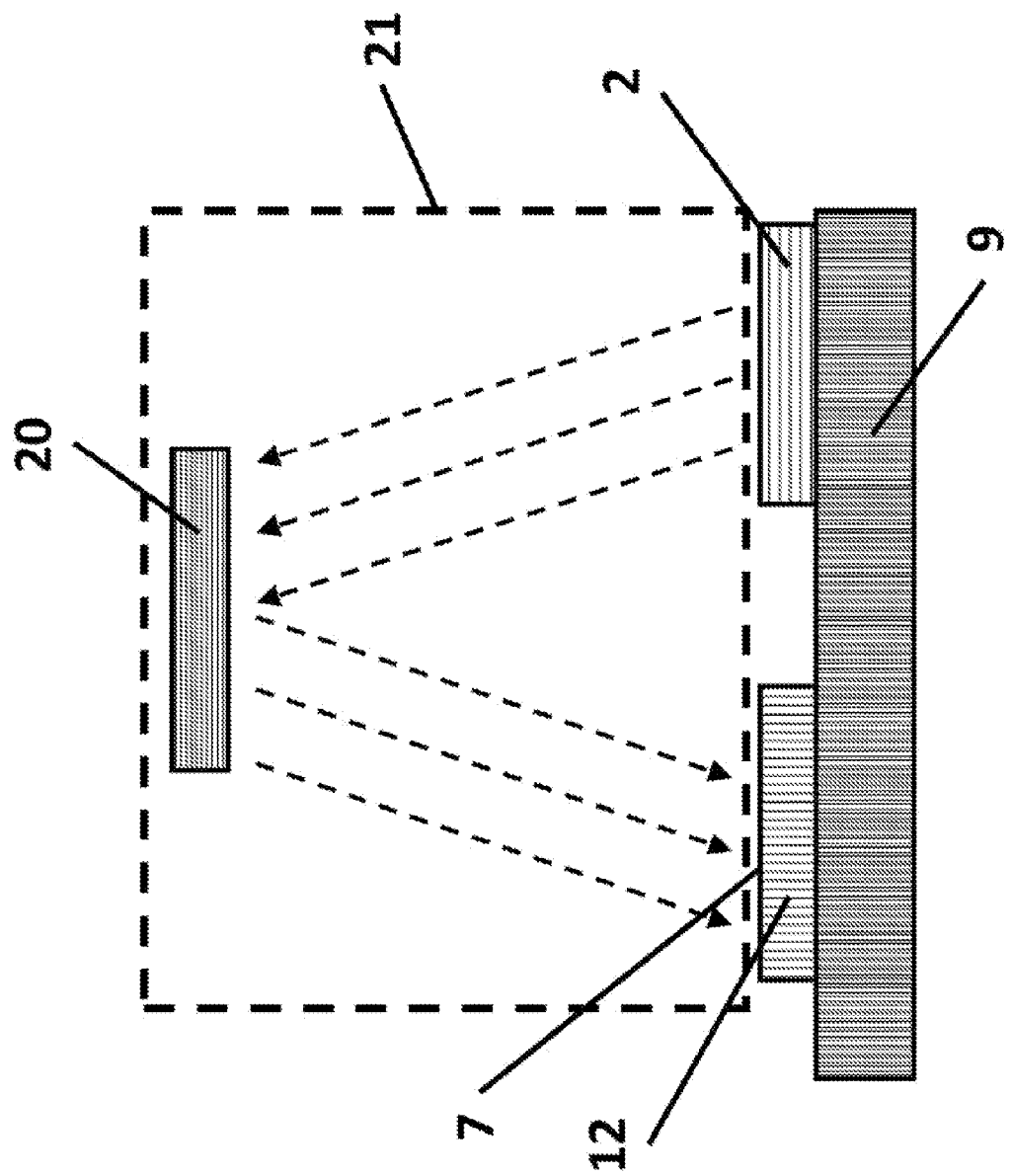
FIG. 4 is a cross sectional side view showing a light source 2 positioned on the PCB 9 and a reflector 20 placed on the ceiling of the casing 11 above the IC 12 that may reflect the light originating from the light source 2 onto the surface 7 of the IC 12.

The optical module 21 may include one or more reflectors 20, one or more lenses, one or more optical fibers, one or more light pipes, and any other component or combination of components capable of directing light. For example, as shown in FIG. 4, the light source 2 may be positioned on or integrated into the PCB 9 and a reflector 20 placed on the ceiling of the casing 11 above the IC 12 may reflect the light originating from the light source 2 onto the surface 7 of the IC 12. The light source 2 may be modulated turned on and turned off repeatedly) at a certain frequency, at multiple frequencies, following a certain predetermined or random sequence in time, or combinations thereof. For example, the light source 2 may be turned on for a predetermined amount of time prior to introducing the particles 4 in order to calibrate the optical sensors 40 on the IC 12 (e.g., by measuring the sensitivity, sensitivity distribution, saturation level, and other relevant parameters of the optical sensors 40 and underlying electronic circuits) and to calibrate the light source 2 (e.g., measure and adjust the light intensity, light uniformity, and other relevant parameters of the light source 2). Subsequently, the light source 2 may be turned on for a predetermined amount of time to allow for a shadow or any other form of light modulation to be created by the particles 4 and detected by the optical sensors 40.

The IC 12 can be a substrate that can incorporate one or more optical sensors 40 and associated electronic circuits. At least a portion of the surface 7 of the IC 12 is coated with receptors and the IC 12 is configured to accept particles 4 that may bind specifically (i.e., via the receptors) or non-specifically to the surface 7 of the IC 12, depending on the concentration of the target analyte. The IC 12 may be used to remove any non-specifically binding particles and quantify the number or concentration of remaining specifically bound particles. The number of specifically bound particles may be proportional to the concentration of the target analyte in the sample. Generally speaking, specifically bound particles are particles that are bound to a surface 7 via at least one specific bond (i.e., antibody-antigen bonds). Generally speaking, non-specifically bound particles are particles that are bound to the surface 7 with weaker bonds (e.g., Van Der Walls). Specifically bound particles refer to particles that are bound with one or more specific biochemical bonds such as one or more immunological bonds and other bonds discussed above and are not removed from the surface 7 by separation forces. Non-specifically bound particles may be particles that are removed from the optical sensing area 41 by separation forces. Non-specifically bound particles may still contain one or more specific bonds but generally contain less specific bonds than specifically bound magnetic particles. For example, for large particles (e.g., those greater than 100 nanometers in diameter), multiple specific bonds may be required for the particles to remain stationary in the presence of separation forces (i.e., to be considered specifically-bound). For example, particles with 10 or more immunological bands may be never removed with separation forces and thus are always considered specifically bound, particles with fewer than one immunological bond may be always removed with separation forces and thus are considered non-specifically bound, whereas particles in between may be either specifically-bound or non-specifically bound. The optical sensors 40 on the IC 12 are configured to detect the shadow cast by the particles, as described above.

Particles may serve as light concentrators through internal or external reflections. For example, the amount of light incident on optical sensors 40 may be increased by over 1% and optical sensors 40 on the IC can be configured to detect this light intensity increase. The particles may modulate the light (e.g., filter the frequency spectrum of the light, fluoresce with another frequency of light, change the color of the light). Likewise, the optical sensors 40 may be configured to detect any of these color changes, for example by using bayer color filter arrays placed over the optical sensors 40 or by using different optical sensor 40 types such as N-well diodes, N+ diodes, poly gate diodes, and P+ diodes, which are sensitive to different optical frequencies. The electronic circuits may be any combination of metal connections, resistors, capacitors, inductors, transistors, diodes, amplifiers, digitizers, digital logic, and other integrated electronic circuits used to obtain, forward, process, and output a signal from the optical sensors 40. The circuitry may be used to individually address any of the optical sensors 40 in an array, either serially or in parallel. The IC may be fabricated in any commercial process (e.g., CMOS, CCD, BJT) or may be made in a custom fabrication process. Other variations, components, and functions of the IC 12 are further described below.

The PCB 9 can be any substrate that stores the IC 12 and connects the IC 12 to any other components. The PCB 9 can contain one or more batteries, one or more control modules, one or more voltage regulators, one or more sensors, one or more actuators, one or more displays, and combinations thereof. As discussed above, the PCB 9 may also include the light source 2 that can provide light into the IC 12 via an optical module 21. The PCB 9 may be placed on the bottom of the housing or in any other position in the housing and may contain connectors and daughter-boards or any other extensions that may contain any of the components described above or described below in any position and orientation inside or outside the housing containing the SPDM 8. The PCB 9 components internal to the system 10 and the circuitry and sensors of the IC 12 may be controlled by a control module integrated on the IC 12 (e.g., a control module core, a discrete control module mounted on the PCB 9, a central processing unit (CPU), a digital signal processing (DSP) unit, a field-programmable gate array (FPGA), or any other control module or combination of control modules). The terms control module and control module may be used interchangeably in this specification and may be located on the PCB 9, in the IC, or in any other part of the system 10. The control module may store assay calibration parameters. Assay calibration parameters may include a standard curve that relates the number or concentration of particles 4 detected to the concentration and/or amount of the target analyte in the aqueous sample 5. Assay calibration parameters may also include an assay time which may include any time intervals between different steps in an assay (e.g., time from aqueous sample 5 detection to optical sensor array readout, readout duration, magnetic separation force duration, and any other time interval). Assay calibration parameters may also include magnetic separation force and magnetic concentration force strength, duration, frequency, pattern. Assay calibration parameters may include any other parameters that may affect assay results. The assay calibration parameters are adjusted in response to measurements made by any sensors and components of the system 10.

The system 10 can contain one or more inertial sensors. The inertial sensors may include accelerometers, gyroscopes, tilt sensors, and any other sensors capable of detecting and quantifying position, velocity, acceleration, orientation, and combinations thereof. The inertial sensors are configured to sense the physical parameters discussed above and output them to the control module. The control module may be configured to read the output from the inertial sensors and determine if any of the physical parameters are unusual and/or out of the acceptable range. For example, the inertial sensors may send an output to the control module indicating that the orientation of the system 10 is incorrect (e.g., the IC 12 is upside down while the assay is being performed) or the acceleration of the system 10 is too high (e.g., a user is shaking or swinging the system 10 while the assay is being performed). As a result, the control module may send a signal to the user via 102 the display 1 that an incorrect action took place and that the results of the assay are invalid. Alternatively, the control module may attempt to compensate for any effects resulting from incorrect orientation and/or applied acceleration. The control module can modify and/or selects the assay calibration parameters based on the measured values of relevant physical parameters. The control module can perform more detailed compensation on the sensor level, for example, by applying different weights to signals from different optical sensors 40 positioned in different locations on the IC, or completely ignoring the reading from certain optical sensors 40 altogether. The control module may also modify the assay time based on the reading obtained from the inertial sensors (e.g., the optical detection may be turned on sooner/later, allowing particles 4 less/more time to incubate with the target analyte, respectively). The inertial sensors may be mounted in any component of the system 10 (e.g., mounted as a chip on the PCB 9, integrated into the IC, mounted on any wall of the casing 11, or combinations thereof).

The PCB 9 and/or the IC 12 may contain a read-only memory module (ROM), a random access memory module (e.g., SRAM, DRAM), or other module capable of storing data (PROM, EPROM, EEPROM, Flash, and any other storage medium). The data module may be part of the control module and may be used to store calibration data from the various sensors, actuators, and modules in the system 10 that is derived just prior, during, or after performing an assay. The data module may store calibration data generated during the design process or after the IC 12 is manufactured and/or the system 10 is assembled. For example, the calibration data may compensate for variations in manufacturing (e.g., ILD thickness, optical sensor 40 sensitivity, and other parameters that may vary during manufacturing). In another example, the calibration data may compensate for variations in surface coating (e.g., surface chemistry, receptor density, receptor type, and other parameters that can vary during surface 7 coating). The calibration data can include assay calibration parameters that are derived from one or more chips in a particular batch (e.g., from the same wafer, same surface coating batch, same assembly batch).

The system 10 can include one or more temperature sensors. The temperature sensors may include a thermistor, a semiconductor sensor, a thermocouple, or combinations thereof, and may be configured to measure the temperature of the surroundings (e.g., the air temperature outside the system 10, the temperature of the SPDM 8, and/or the temperature in the vicinity of the IC 12) or the temperature of the aqueous sample 5 directly (e.g., the SPDM 8 may be configured to place the temperature sensor in contact with the aqueous sample 5, or the sensor may be located at or near the surface 7 of the IC 12). An assay may have different assay calibration parameters (e.g., different standard curve, different suitable assay time) at each temperature level and as the assay kinetics may be sped up or slowed down depending on the temperature level. Accordingly, the temperature reading may be sent to the control module and may be used to adjust the assay calibration parameters to compensate for the changes in temperature. Aside from being integrated or attached to the PCB 9, the temperature sensor may be mounted in any other component of the system 10 (e.g., integrated into the IC 12, mounted on any wall of the casing 11, or combinations thereof). The IC 12 may contain one or more heating elements (e.g., resistors, coils, wires) that can be used to keep the temperature of the surface 7 of the IC 12, the aqueous sample 5, and/or the entire system 10 at a nearly constant, predetermined value. The information from the temperature sensors can be read and the control module can enable the heating elements in order to keep the temperature constant in the range of 20° C.-40° C.

The system 10 can include one or more moisture sensors. The moisture sensor(s) may be placed in contact with the aqueous sample 5 and may be used to detect the presence of the aqueous sample 5 (e.g., using electrodes to detect a change in resistance or a change in capacitance between the electrodes as a result of the presence of the aqueous sample 5). The moisture sensor(s) may send a signal to the control module, either continuously or upon detection of the aqueous sample 5, indicating the moisture level reading, and the control module may enable other components of the system 10 upon receiving a signal indicating the presence of the aqueous sample 5. Aside from being integrated or attached to the PCB 9, the moisture sensor may be mounted in any other component of the system 10 (e.g., integrated into the IC 12, mounted on any wall of the casing 11, or combinations thereof).

The PCB 9 can include one or more viscosity sensors. A viscosity sensor can be placed in contact with the aqueous sample 5. The viscosity of blood plasma can vary. Higher fluid viscosities may lead to longer assay kinetics and longer particle sedimentation times. Accordingly, the viscosity sensor(s) may send a measurement of the viscosity to the control module which in turn may modify the assay time other assay calibration parameters. Aside from being integrated or attached to the PCB 9, the viscosity sensor(s) may be mounted in any other component of the system 10 (e.g., integrated into the IC 12, mounted on any wall of the casing 11, or combinations thereof). By including temperature, viscosity, orientation, acceleration, and any other environmental factors into account when performing an assay, the results of the assay may be adjusted appropriately, via the assay calibration parameters, to effectively cancel out these environmental effects, leading to increased robustness, accuracy, and consistency of results in diverse environments and settings. The moisture sensors placed at different points along the path of the aqueous sample 5 can be used to measure the viscosity of the fluid. Alternatively or in combination, the optical sensors 40 can be used to measure the time from the reagent sphere 3 re-hydrating to the time the particles 4 sediment onto the surface 7 of the IC 12. This time can also be used to determine the viscosity and incubation time information.

The system 10 can include a vibrator module. The vibrator module may include an electric motor with an unbalanced mass or any other module and method for generating vibrations. The vibrator module may be turned on during the sample delivery steps (i.e., between the time when the aqueous sample 5 is introduced and the time the particles 4 finish sedimenting on the surface 7 of the IC 12) in order to agitate the aqueous sample 5 and/or the particles 4 and allow the particles 4 to more quickly disperse in the aqueous sample 5 and speed up assay kinetics. The vibrator module may be enabled upon detection of the aqueous sample 5 when the aqueous sample 5 comes in contact with the SPDM 8 and/or the IC. The amplitude, frequency, and/or pattern of the vibrations can be controlled by the control module and adjusted based on various parameters obtained from the environmental sensors discussed above and based on any assay calibration parameters. For example, vibration amplitude may be increased if the temperature is low and/or the viscosity of the aqueous sample 5 is high in order to speed up assay kinetics.

The PCB 9 can contain one or more external electromagnets or permanent magnets generating fields from 0.1 µT to 1 T at excitation frequencies from DC to 100 MHz. Magnets can have an appreciable effect on the particles 4 if the particles 4 are magnetic particles 81. A permanent magnet may be placed below the IC 12 or in close proximity to the IC 12 in order to pull magnetic particles 81 more quickly towards the surface 7 of the IC 12 (i.e., increase the sedimentation velocity of the magnetic particles 81 to as high as 10 mm per second). The permanent magnet may be replaced with an electromagnet (e.g., Helmholtz coil, current line, or combinations thereof) mounted onto the PCB 9 and below the IC 12 to selectively generate magnetic fields and magnetic forces. A second electromagnet may be placed above the IC 12, near the ceiling of the casing 11, in order to pull the magnetic particles 81 up from the sensor surface 7. This could be used to increase the incubation time to over 10 minutes or to perform magnetic separation steps. One or more electromagnets may be placed on the sides of the PCB 9 around the sample chamber or extend into the system 10 and around the sample chamber in order to generate lateral forces on the magnetic particles 81. Any of the electromagnets placed above, below, or to the sides of the sample chamber may be used to agitate the magnetic particles 81 (e.g., move them side to side, make them vibrate, make them change orientation) in order to create convective forces in the aqueous sample 5 and/or to more quickly sediment the magnetic particles 81 to the IC 12 surface 7. Electromagnets configured to generate lateral forces may be used to compensate any tilt in the system 10 (e.g., if the system 10 is tilted to the left, an electromagnet on the right side may turn on to ensure magnetic particles 81 sediment evenly and do not aggregate on the left side of the IC). The permanent magnets or electromagnets may be mounted in any other component of the system 10 (e.g., integrated into the IC, mounted on any wall of the casing 11, or combinations thereof).

The display 1 can be any display known in the prior art (e.g., LCD display, LED display, OLED display and any other type of display) that may show the results of an assay (e.g., concentration of the target analyte, amount of the target analyte, and any other relevant results). The display 1 may show status indicators (e.g., ready, busy, testing, done) and may show visual instructions to the user on how to use the system 10 to perform a measurement. A speaker may also be integrated into the system 10 to deliver audio instructions.

The casing 11 can be an external shell that houses all the other components of the system 10. The casing 11 may be made in any standard or custom manufacturing process (e.g., injection molding) and may be made from any standard material (e.g., plastic).

FIGS. 5A and 5B shows a cross section view and top view, respectively, of the light source 2 and the IC 12. The IC 12 can include one or more optical sensors 40 configured in an array. Each optical sensor 40 may be integrated into the IC 12 and implemented in any technology (e.g., junction photodiodes, avalanche photodiodes, PIN photodiodes, active pixel sensors, charge-coupled devices, light-sensitive resistors, or other solid-state optical sensors 40). Each optical sensor 40 may be individually addressable and may output electrical signals that may be amplified, digitized, stored and processed by circuitry on the IC 12 and/or the PCB 9. Each optical sensor 40 may be configured to detect a shadow 34 cast by a particle 4 as a result of the particle blocking the light rays from the light source 2. For example, optical sensor 30 detects particle 32 because particle 32 casts a shadow 34 over the sensor 30, decreasing the light intensity incident on optical sensor 30 from the light source 2. Consequently, as a result of particle 32 blocking a portion of the light from the light source 2, optical sensor 30 generates a signal that is different from a baseline signal without particle 32, thus indicating the presence of particle 32 over the sensor. On the other hand, optical sensor 31 does not detect a particle as no light is blocked from the light source 2. Other types of light modulation may be employed to detect particles 4. For example, the particles 4 can be made to modify the spectral composition (e.g. color) of the light, and the optical sensors 40 may be configured to detect such modification, thus detecting the presence of beads near the sensor. The optical sensing area 41 corresponds to the area on the surface 7 of the integrated circuit 12 where optical sensors 40 can detect the presence of particles 4. The optical sensing area 41 may be a column of optical sensors 40 and several columns of optical sensors 40 may be placed adjacent to each other to create a large array of optical sensors 40. The column of optical sensors 40 can include separation and concentration conductors. The columns of optical sensors 40 can be placed at a distance from each other to leave space in between the column to separate the non-specifically bound magnetic particles.

Depending on the size of an optical sensor 40 and the particles 4 used, each optical sensor 40 can detect one or more particles 4 or several optical sensors 40 can detect the same single particle 4. In general, the optical sensors 40 can be square and range from 0.1 µm to 200 µm on a side. A preferable side length for an optical sensor 40 designed for detecting micron-sized particles may range between 0.5 µm and 10 µm. Additionally, the optical sensors 40 can be any shape such as triangular, circular, rectangular, or any other polygon or combination thereof. An optical sensor 40 significantly larger than a particle 4 may generate a signal proportional to the number and/or density of particles residing over its surface. Conversely, optical sensors 40 smaller than one particle 4 may generate signals indicating the portion and/or orientation of a particle 4 residing over the surface 7 containing these optical sensors 40. Optical sensors 40 may be made small enough and packed densely enough to guarantee that no matter where a particle 4 lands in the optical sensing area 41, that particle is always detected by at least one optical sensor. For example, a 2-dimensional array of 4 µm×4 µm square optical sensors 40 with a pitch between their centers of 4.5 µm may detect all 4.5 µm particles 4 that land in the optical sensing area 41. Individual detection of particles 4 may enable detection contrast ratios down to 1% resulting in an increased signal to noise ratio; thus the design of the readout electronics in the IC 12 and/or PCB 9 may be greatly simplified.

One or more reference sensors (not shown) may be implemented on the IC. Reference sensors may be similar to optical sensors 40 discussed above and may be matched in size, orientation, and may be surrounded by a similar environment (e.g., both reference sensors and optical sensors 40 may be surrounded by the same dummy structures, same magnetic field generators). Reference sensors can be covered fully or partially by poly-silicon layers, metal layers, other substantially opaque materials or combinations thereof such that no light, or a relatively small amount of light, or a pre-determined amount light from the light source 2 is incident on the reference sensors. The reference sensors, such as the optical sensors 40 covered by material to block the light from the light source 2, may be used to measure the dark current of the associated photodiodes which may be used for calibration and offset cancellation purposes, for example, when placed in differential configuration with an optical sensor 40 that is exposed to the light source 2. Reference sensors can be identical to the optical sensors 40 but the system 10 can be configured to prevent particles 4 from landing over them (e.g., the reference sensors may be in a chamber with no particles, particles may be removed from the reference sensors by very strong forces, or any other configurations of ensuring that the surface 7 of these reference sensors is not covered by particles). Reference sensors may be used to measure the ambient light intensity which may be used for calibration and/or offset cancellation purposes.

FIG. 6 shows a cross section view of the IC. Optical sensing areas (e.g., Optical sensing area 1 50 and Optical sensing area 2 51) may be post processed so that the plane of the optical sensing areas is positioned below that of the rest of the IC 12 (e.g., in trench 52 and trench 53) in order to allow more light to reach the optical sensors 40 and to minimize light scattering that may effectively degrade shadows or other modulation of the light due to particles 4. The etching process is described in PCT Publication No. WO 2009/091926. A metal etch stop layer above the optical sensor 40 can be used to stop the etching process. Once the silicon dioxide is etched away from above the etch stop metal layer, the metal layer and the metal strap can be etched to expose the silicon dioxide underneath, leaving only a transparent layer of silicon oxide. An IC 12 can have more than one optical sensing area 41. Each optical sensing area 41 may be coated with a different receptor that is specific to a unique target analyte. For example, the surface 54 of trench 52 may be coated to capture one analyte while the surface 55 of trench 53 may be coated to capture another analyte. Having a separate trenches for each receptor may prevent cross-contamination of receptors during coating (e.g., prevent droplets from mixing during a micro-spotting process), as is often the case in systems with flat topologies. Coffee ring effects (e.g. non-uniform concentration of the reagents and/or receptors) may be avoided or reduced by coating the surface in trenches. Each trench may have its own reaction chamber. For example, trench 52 may be isolated from trench 53 by a capillary wall above the boundary between the two trenches such that the aqueous sample 5 in contact with trench 52 does not mix with the aqueous sample 5 in contact with trench 53. Particles 4 in each trench may be coated with different receptors. The surface in a trench may be coated with more than one receptor, either by mixing two or more receptors and coating the whole trench or by coating the surface of the trench with each receptor in different portions of the trench. In one variation of the IC, trenches can be omitted altogether (i.e., the surface 7 of the chip may be essentially flat) and different regions on the IC 12 may be functionalized with different receptors. The detection and/or quantitation of multiple target species can be performed concurrently, for example, by coating different sections or the chip or different trenches with different receptors. The application of different receptors in different trenches can be performed through various micro-arraying techniques, namely contact micro-arraying or print micro-arraying.

Figure 7C:
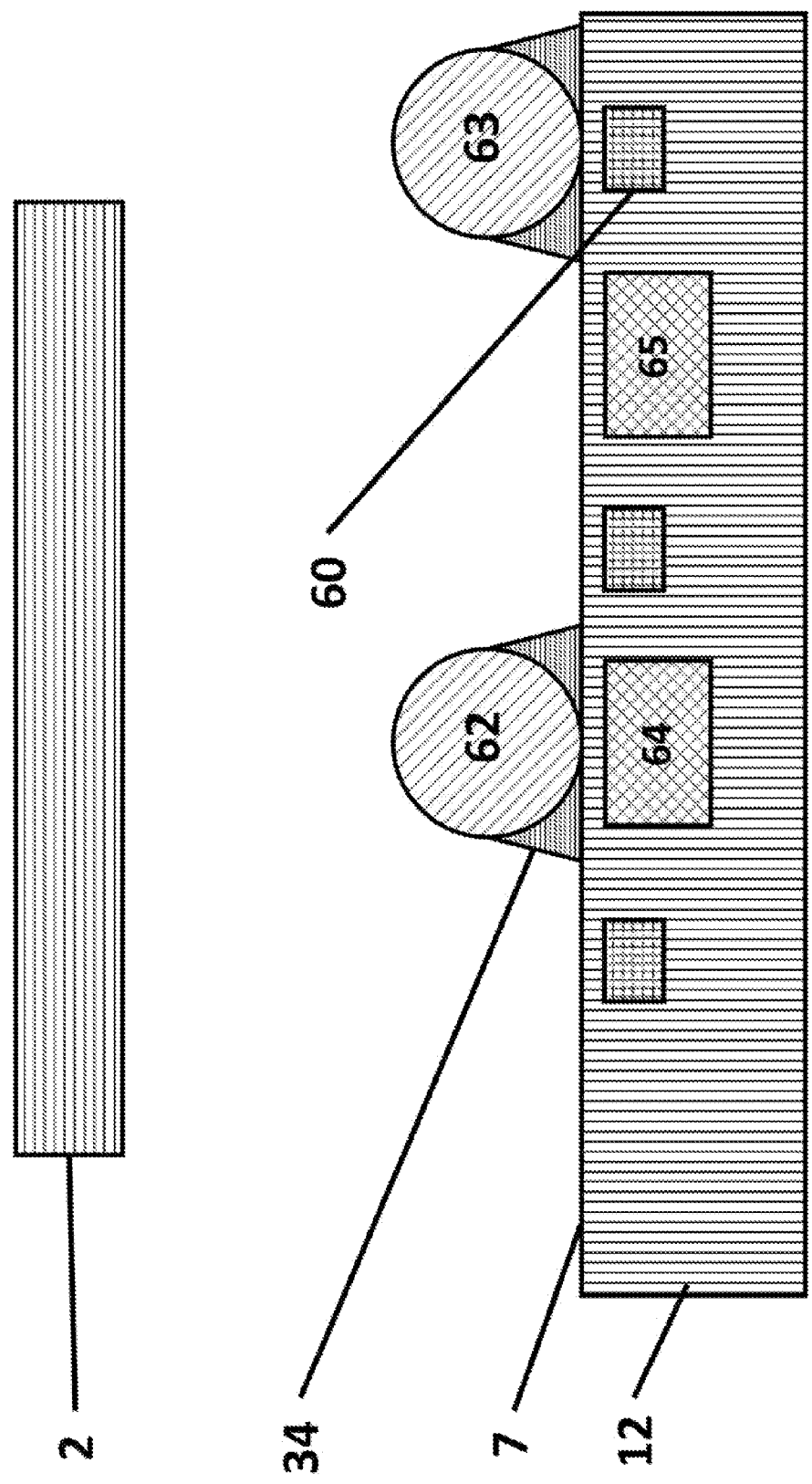
FIG. 7C is a cross-sectional view that presents the scenario from FIGS. 7A and 7B after non-specifically bound magnetic particle 63 is attracted to a separation conductor 60.

FIGS. 7A, 7B, and 7C show a top view and cross sectional views, respectively, of the light source 2 and the IC 12. One or more magnetic separation field generators can be embedded in the integrated circuit 12 at a lateral distance of 0.1 µm to 100 µm from the optical sensing area 41. Magnetic particles 81 that had previously reacted with one or more target species or react with one or more target species found on the surface 7 of the IC 12 may bind strongly through specific bio-chemical or inorganic interactions to the surface 7 of the IC 12 exposed to the aqueous sample 5. Magnetic particles 81 that had not reacted with one or more target species may bind weakly to the surface 7 of the IC 12 through non-specific interactions. The magnetic separation field generators can be used to remove the non-specifically bound magnetic particles from the optical sensing areas 41 so that the optical sensors 40 only detect specifically bound magnetic particles. The magnetic separation field generators can be implemented as electrical separation conductors 60 embedded in the integrated circuit 12 and routed in proximity to the optical sensing area 41. Current passing through the separation conductors generates magnetic forces that act on the magnetic particles 81 inside the optical sensing area. The current can be from 0.01 mA to 200 mA depending on the separation force desired. A preferable value for the current passing though separation conductors to separate 4.5 µm magnetic particles ranges from 1 mA to 50 mA. The separation conductors 60 on either side of the optical sensing area 41 can be activated at different times in order to pull the magnetic particles 81. The current can be toggled between the two separation conductors at arbitrary frequency from 0.001 Hz to 100 MHz. The magnetic separation forces can be strong enough to displace non-specifically bound magnetic particles from the optical sensing area towards the separation conductor, but not strong enough to displace specifically bound magnetic particles. Non-specific binding forces may be on the order of 0.1-10 pN, while specific binding forces may be on the order of 20 pN to 20 nN. For example, magnetic particle 62 may sediment over optical sensor 64 and may specifically bind to the surface 7 of the IC 12 over optical sensor 64. Thus, magnetic particle 62 may not be removed by the separation force generated by a separation conductor 60 placed laterally to the optical sensing area 41 and may be detected by optical sensor 64. On the other hand, magnetic particle 63 may sediment over optical sensor 65 and may not bind specifically (i.e., non-specifically bind) to the surface 7 of the IC 12 over optical sensor 65. Thus, magnetic particle 63 may be removed by the separation force generated by the conductors placed laterally to the optical sensing area 41 and may not be detected by optical sensor 65. The electric currents used to generate magnetic forces may be pre-programmed onto the IC 12 during the design process or after fabrication and may be adjusted at a later stage (e.g., before the assay or dynamically during the operation of the assay) depending on various parameters (e.g., temperature, viscosity of the aqueous sample 5, magnetic content of the magnetic particles, size/shape of the magnetic particles, and other factors). Magnetic forces can be generated externally to the integrated circuit 12 using one or more permanent magnets or external electromagnets (e.g., coils integrated onto the PCB 9). In a variation of the system 10, magnetic separation field generators may be omitted altogether from the IC 12.

Figure 8A:
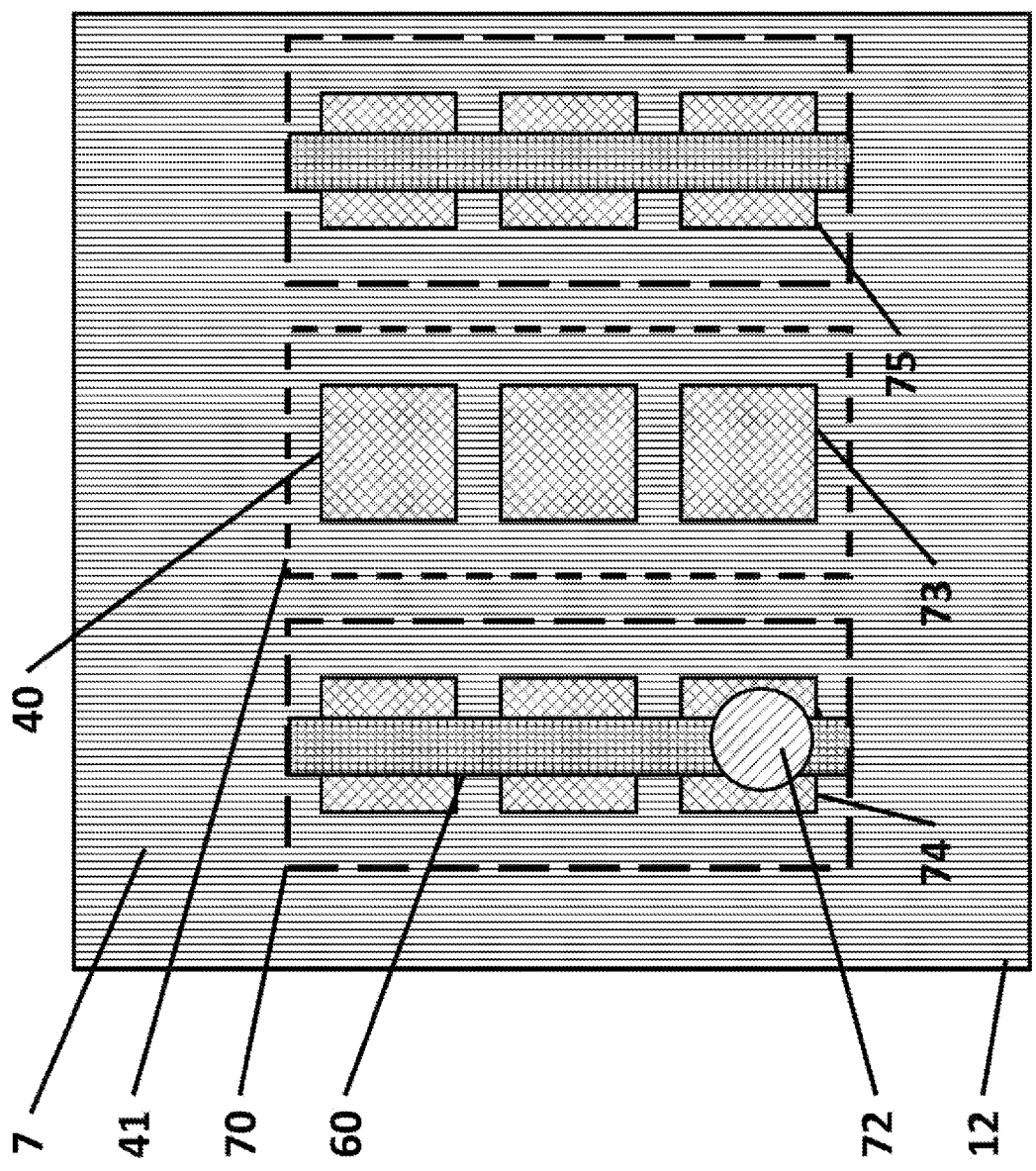
FIGS. 8A and 8B are top and cross sectional side views, respectively, of a variation of the IC 12 that can have optical sensors 40 in a separation area 70.
Figure 8B:
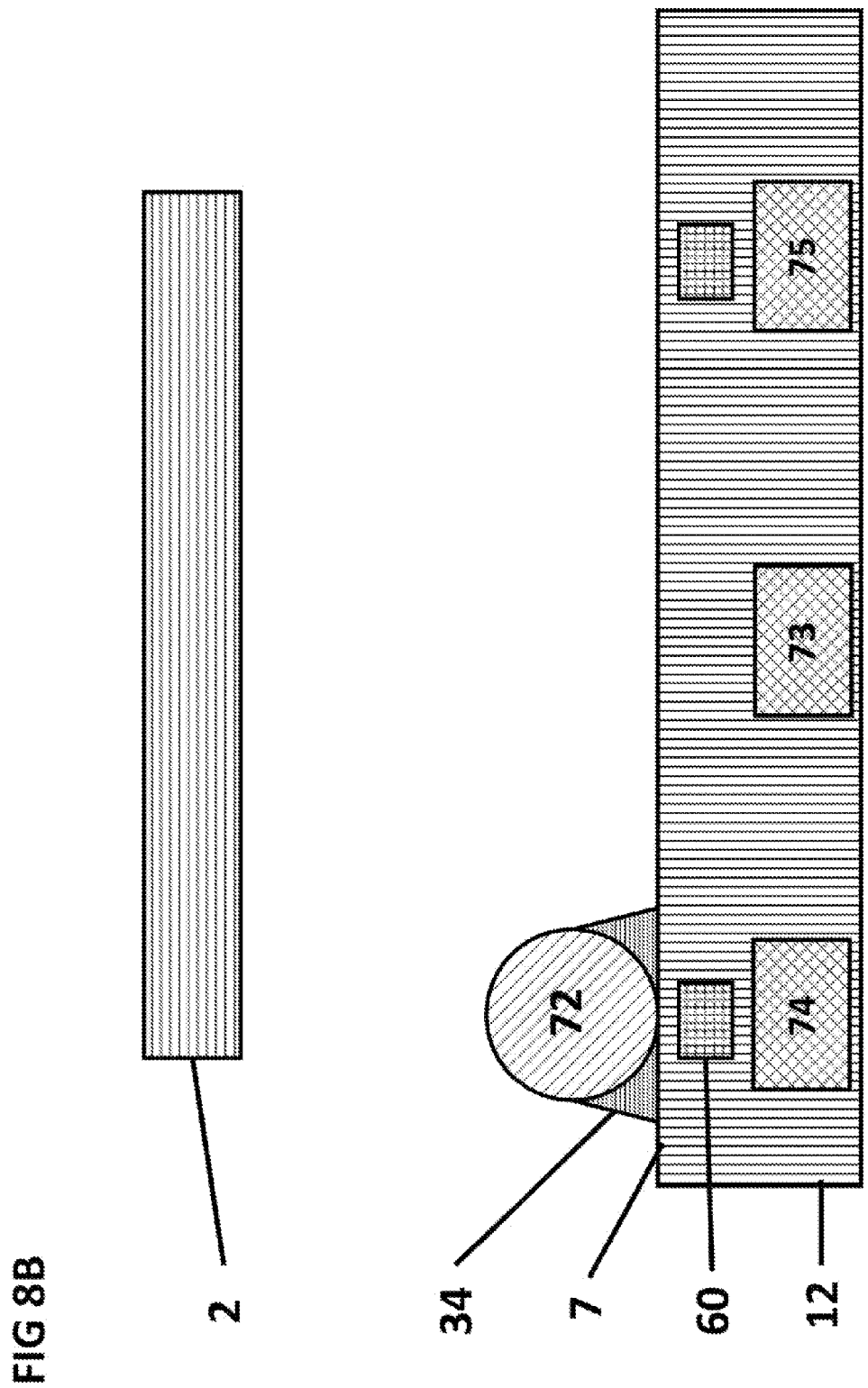

FIGS. 8A and 8B show a top view and a cross section view, respectively, of the light source 2 and the IC 12. Magnetic separation field generators can be embedded in the IC 12 at a lateral distance of 0.1 µm to 100 µm from the optical sensing area 41. A separation area 70 over the magnetic separation conductors 60 may contain optical sensors 40 for detecting magnetic particles 81. Magnetic forces generated by separation conductors 60 may remove non-specifically bound magnetic particle 72 from the optical sensing area 41 and onto the separation area 70. Optical sensor 74 in the separation area 70 may be used to determine the efficacy of magnetic concentration field generators, described further below in reference to FIGS. 9A and 9B. Since magnetic concentration field generators should concentrate more magnetic particles 81 over the optical sensing area 41 than over the nearby separation areas 70, calculating a concentration ratio, defined as the number and/or density of magnetic particles 81 sedimented in the optical sensing area 41 divided by the number and/or density of magnetic particles 81 sedimented in the separation area 70, may verify and measure the efficacy of the magnetic concentration field generators. It is preferable that the concentration ratio is between 2:1 to 100:1.

In addition to quantifying the number of remaining specifically bound magnetic particles in the optical sensing area 41, the number and/or density of magnetic particles removed from the optical sensing area 41 may be quantified or estimated by the optical sensors 40 in the separation area 70, thus giving an estimate of the total number of magnetic particles sedimenting on the IC 12 surface 7. This facilitates a calculation (e.g., by the control module) of a ratio of magnetic particles removed and/or magnetic particles remaining compared to the total number of magnetic particles. Measuring this ratio or the percentage of particles specifically binding to the surface 7 may correct for various errors, such as those stemming from variations in the total amount of magnetic particles introduced to the IC 12 surface 7, which may be different between systems, and any other error sources such as improper use, manufacturing detects, or combinations thereof. Another method for calculating this ratio is to quantify the number magnetic particles in the optical sensing areas 41 both before and after magnetic separation. This method allows the magnetic separation areas 70 to be omitted while still obtaining the ratio. Further, the optical sensors in the optical sensing area 41 and the separation area 70 can be used to retrieve ensemble statistics of the magnetic particles 81, such as total number of magnetic particles 81 in the system 10, and the amount of particle 4 clumping.

Figure 9B:
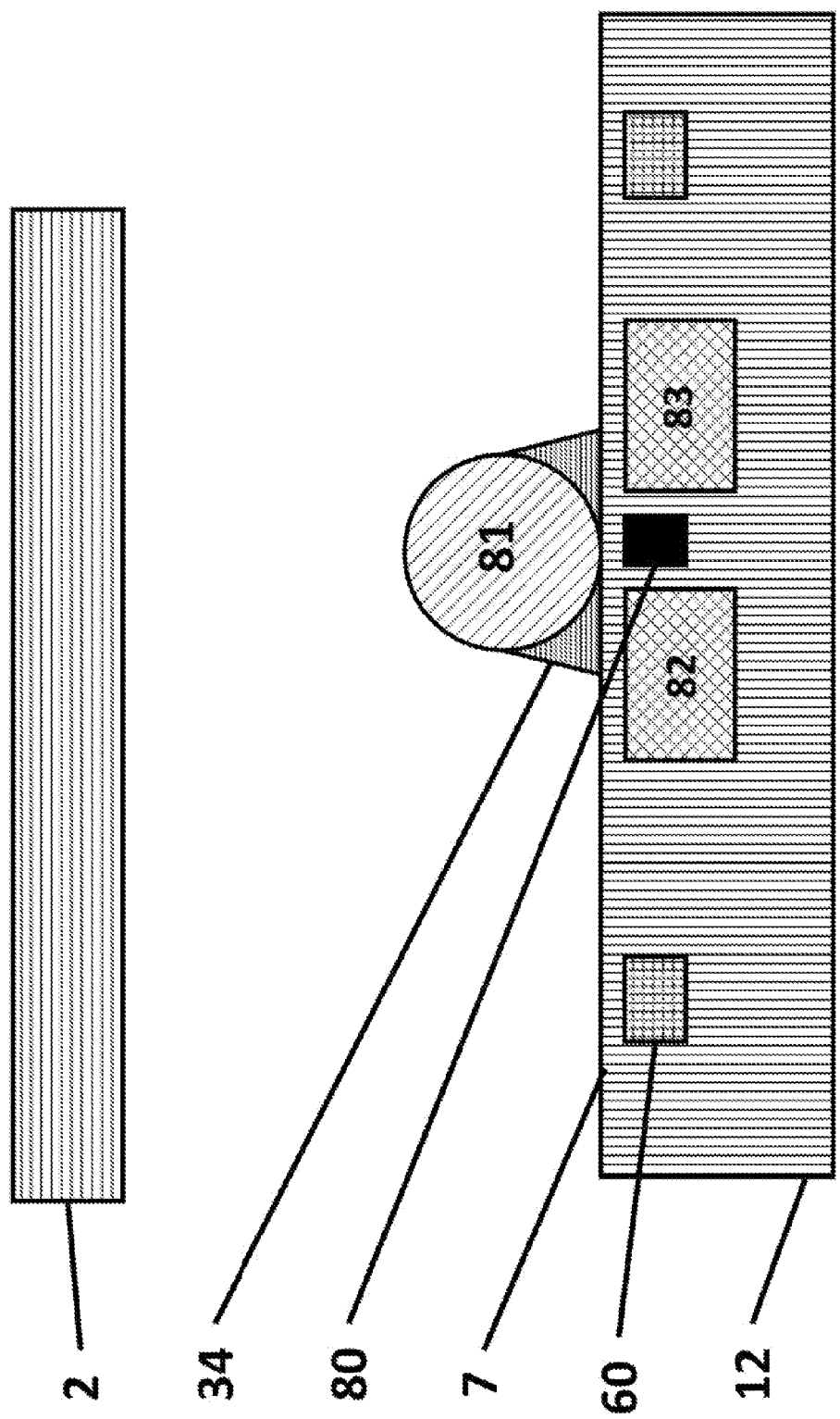

FIGS. 9A and 9B show a top view and a cross sectional side view, respectively, of the light source 2 and the IC. Magnetic concentration field generators embedded in the integrated circuit 12 can be used to attract the magnetic particles 81 onto one or more optical sensing area 41s on the surface 7. The magnetic concentration field generators can be implemented as electrical concentration conductors 80 embedded in the integrated circuit 12 and routed through one or more optical sensing areas 41. Current passing through the concentration conductors 80 may generate magnetic forces that attract the magnetic particles 81 to the surface 7 of one or more optical sensing areas 41. The current flowing through the concentration conductors 80 can range from 10 µA to 200 mA, depending on the strength of magnetic particle concentration force desired. These currents may broadly correspond to magnetic forces from 1 fN to 1 nN, largely depending on the size of magnetic particles 81. Concentrating magnetic particles 81 over the optical sensors 40, rather than allowing them to land randomly on the surface 7, may alter (e.g., increase) the accuracy and/or performance of the assay (e.g., by increasing the chance of magnetic particles 81 binding specifically in the optical sensing area 41). The concentration conductors 80 may speed up the sedimentation process of the magnetic particles 81 and thus decrease the time to perform the assay. In a variation of the IC, the concentration conductors 80 may be omitted altogether. A permanent magnet or an electromagnet (e.g., a coil integrated into the PCB 9) may be used instead of a concentration conductor 80 to concentrate magnetic particles 81 onto the surface 7 of the IC 12.

FIG. 9A shows the concentration conductor 80 in between two columns of optical sensors 40. The concentration conductor 80 can be placed directly over a column of sensors. The magnetic forces generated by concentration conductors 80 may be pre-programmed onto the IC 12 during design of fabrication and may be adjusted at a later stage (e.g., before the assay or dynamically during the operation of the assay) depending on various parameters (e.g., temperature, viscosity of the aqueous sample 5, magnetic content of the magnetic particles 81, size/shape of the magnetic particles 81, and other factors).

Figure 10A:
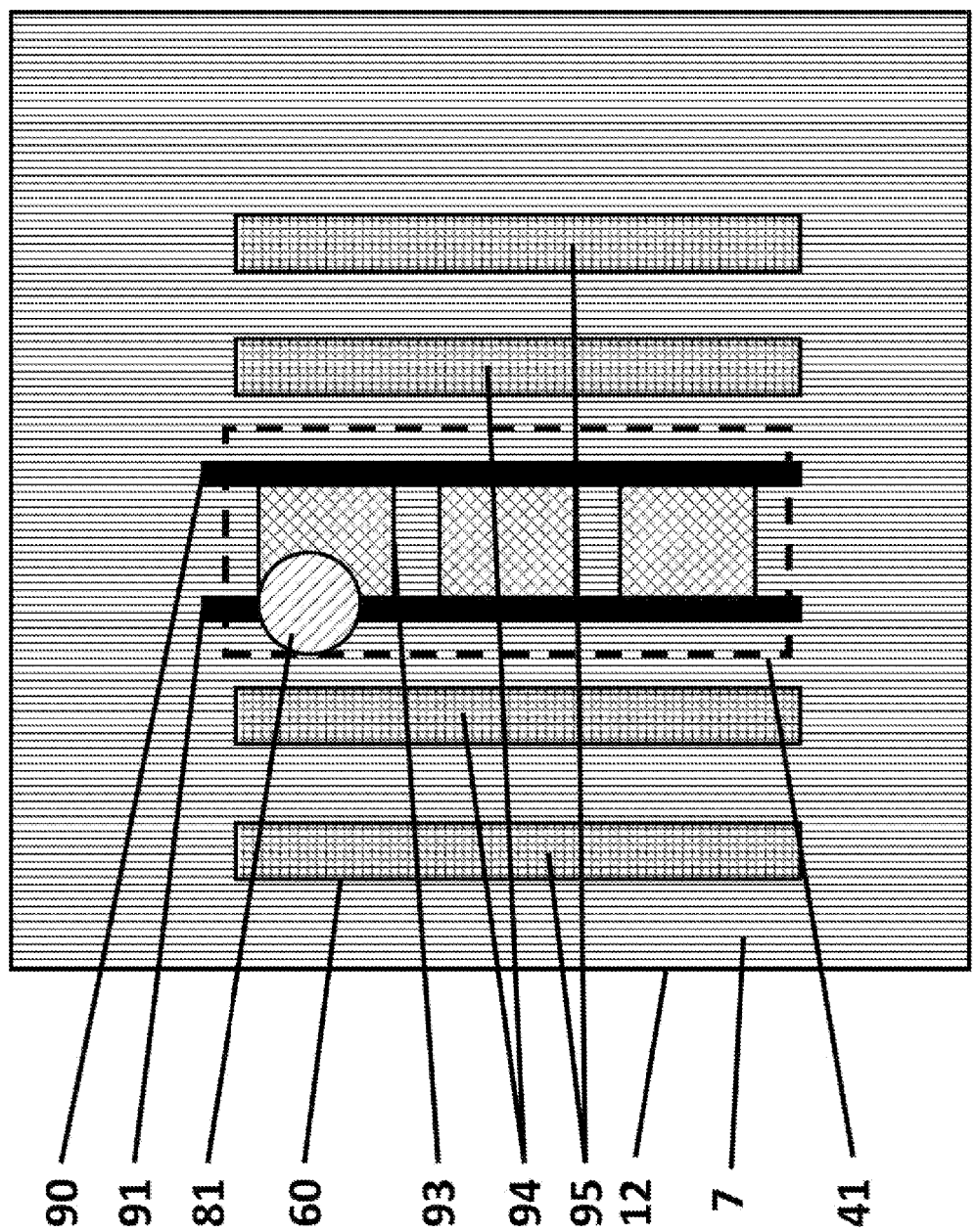
FIGS. 10A and 10B are top and cross sectional side views, respectively, of a variation of the IC 12 that can have a separation conductor 60 and two concentration conductors.
Figure 10B:
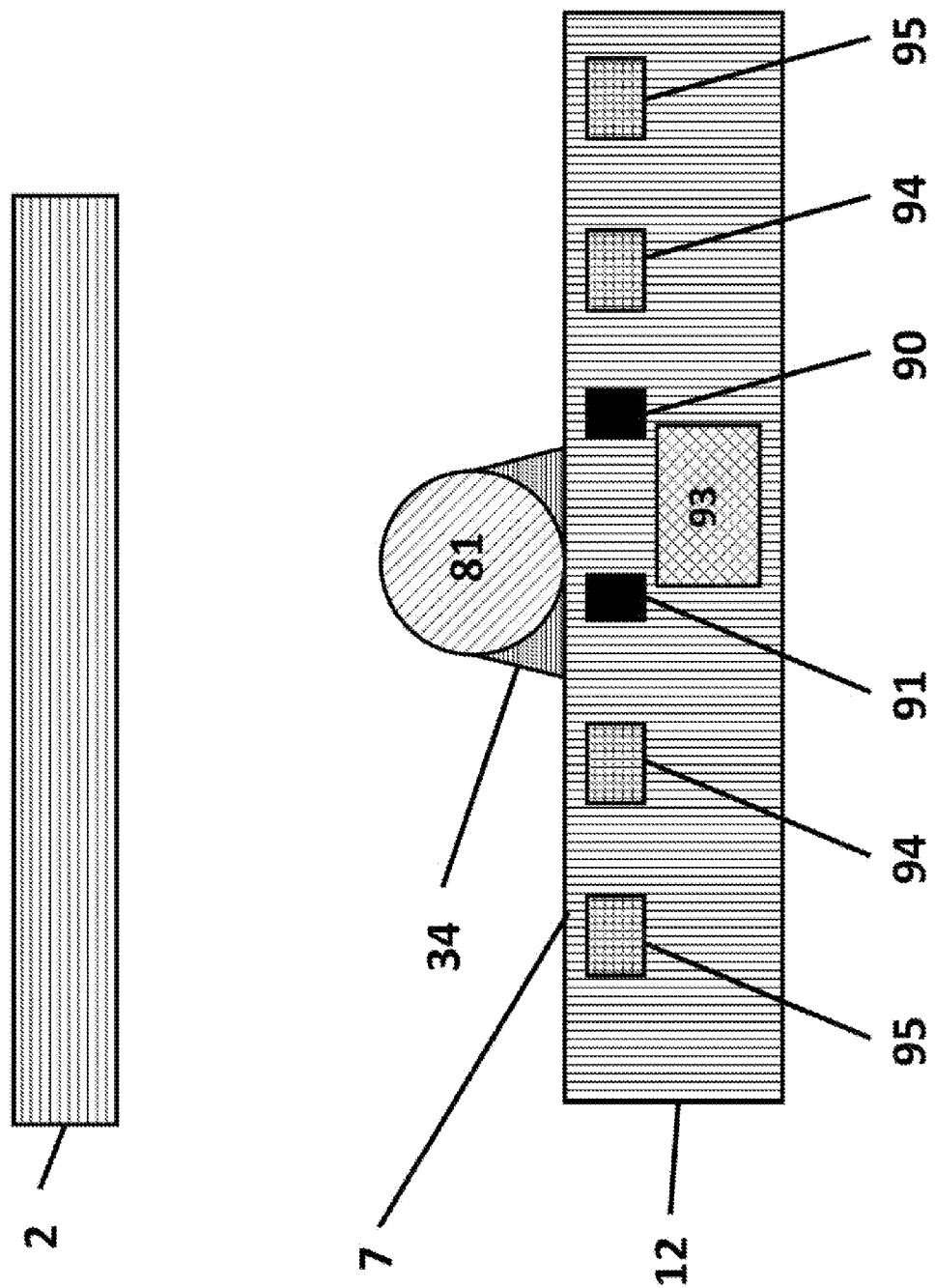

FIGS. 10A and 10B show a top view and a cross section view, respectively, of the light source 2 and the IC 12. Two concentration conductors 80 can be placed over and/or next to one or more optical sensing areas 41. These concentration conductors 80 may be both turned on (i.e., a current passes through both conductors and a magnetic force is generated that is similar to a force from one concentration conductor 80 as described in reference to FIGS. 9A and 9B) in order to concentrate magnetic particles 81 over or next to the optical sensing areas 41. Current may be alternated from one the right concentration conductor 90 to the left concentration conductor 91 (i.e., only one concentration conductor is turned on at a time and the current switches to the other line in a predetermined, calculated, or random time internal). When this happens, a magnetic particle 81 landing on the surface 7 may be rastered across the optical sensing area 41 (i.e., moved back in forth on the surface 7 over an optical sensor 93), thereby increasing the chance that this magnetic particle 81 will specifically bind to the surface 7 of the IC 12. The chance of binding and by extension the sensitivity of the assay increases proportionately with the increase in surface 7 area of the magnetic particle 81 that comes in contact with the optical sensing area 41. More than two concentration conductors may be placed in any orientation as to raster the magnetic particle 81 over an optical sensing area 41 in any fashion. This rastering of the magnetic particles 81 can also be used to eliminate the non-specific binding that can result from the magnetic particles 81 remaining stationary on the surface 7 of the IC 12 for an extended period of time, (e.g., from 1 second to 10 minutes). Two separation conductors 60 can be placed on each side of a column of an optical sensing area 41. The innermost separation conductors 94, which are closest to the optical sensing area 41 may be turned on first to remove non-specifically bound particles from the optical sensing area 41 and attract them towards the innermost separation conductors 94. Only one separation conductor is turned on at one time and the current can be toggled between the two parallels separation conductors 94. Subsequently, the innermost separation conductors 94 closest to the optical sensing area 41 may be turned off and the outermost separation conductors 95 may be turned on to remove non-specifically bound magnetic particles from the innermost separation conductors 94 and attract them towards the outermost separation conductors 95. Only one separation conductor is turned on at one time and the current can be toggled between the two parallels separation conductors 95. More than two separation conductors 60 may be placed in this fashion on each side of a column of optical sensors in order to move the magnetic particles 81 arbitrarily far away from the column of optical sensors. Attracting the magnetic particles 81 to the innermost conductors may require less than 20 mA of separation current, whereas directly attracting magnetic particles 81 from the sensor surface 7 to the outermost conductors may require as much as 3 times more separation current. Stacking or rastering two or more such separation conductors 60 may thus result in a reduction of power dissipation or energy consumption of the IC 12. More combinations of numbers of concentration conductors 80 and separation conductors 60 (e.g., two concentration conductors 80 and four separation conductors 60) may be used for each optical sensing area 41. In one variation of the system 10, magnetic separation field generators may serve as a magnetic concentration field generators (i.e., the magnetic separation field generators may be used to concentrate magnetic particles 81 to or close to the optical sensing areas 41), and magnetic concentration field generators may also serve as magnetic separation field generators (i.e., the magnetic concentration field generators may also be used to remove non-specifically bound magnetic particles 81). Thus, in a variation of the system 10, the magnetic concentration field generators and/or the magnetic separation field generators can be omitted.

Figure 11B:
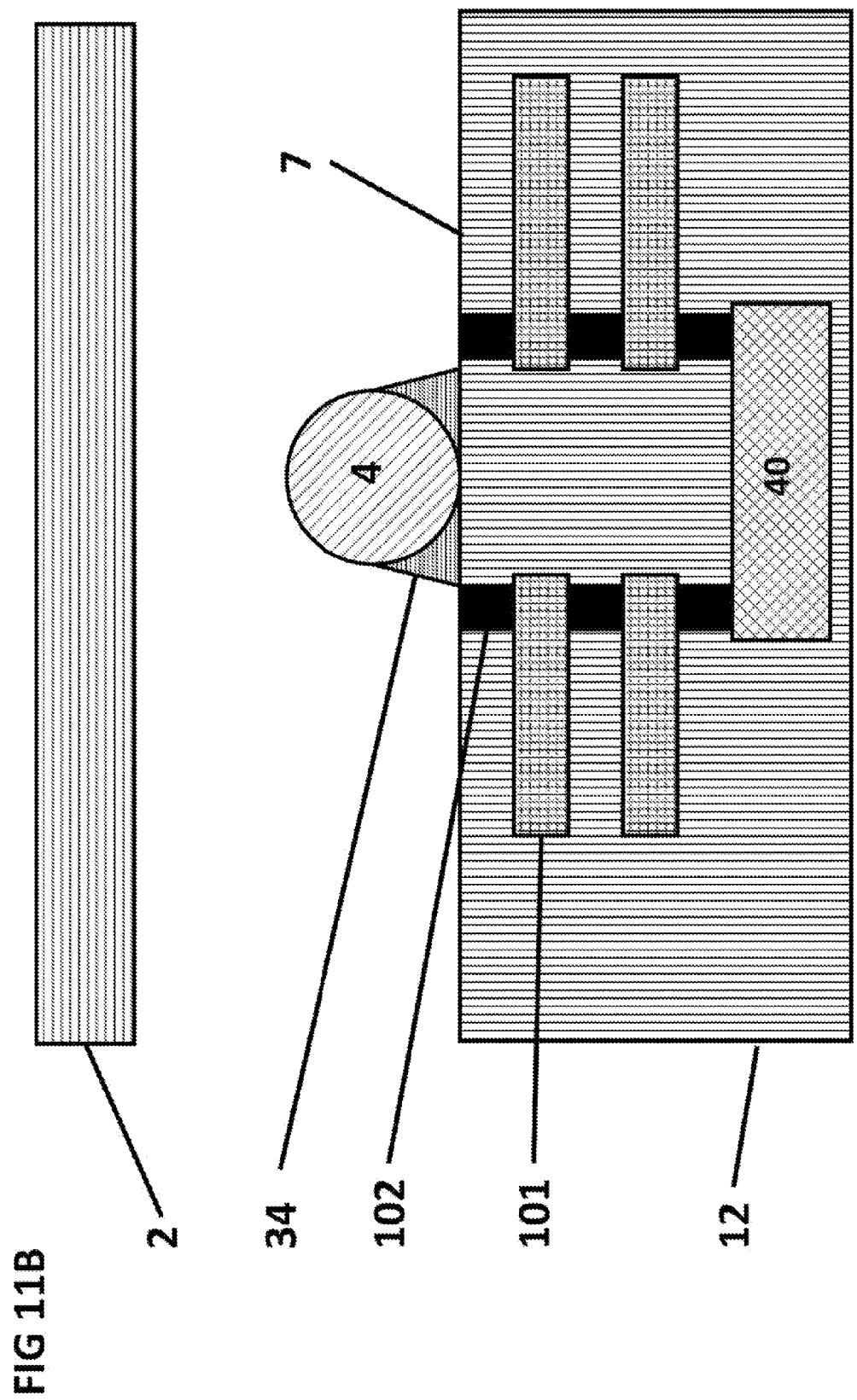

FIGS. 11A and 11B show a top view and a cross section view, respectively, of the light source 2 and the IC 12. Metal, poly-silicon, or other opaque or mostly opaque materials can be integrated into the IC 12 serve as a light shield 101 for the optical sensors. The light shield 101 may surround an optical sensor 40 to reduce the angles of acceptance of light of the optical sensor 40 and reduce stray light (e.g., dispersed, reflected, or refracted light coming from direction or from cross talk from nearby optical sensors) by more than 90%. The light shield 101 may or may not overlap a part of the optical sensor 40 and may be made out of a stack of several layers (e.g., poly-silicon, metal 1, metal 2, and other on-chip metal layers or other opaque layers). To further prevent stray light from shining on the optical sensor 40, the ILD space between the light shield layers 101 may be surrounded by vias 102 connecting each layer together. The vias 102 may be implemented in a standard process (i.e., where they are a predetermined size and/or have a predetermined inter-via spacing) and may surround the optical sensor 40 as densely as possible. Alternatively, the vias 102 may be implemented in a special process and may completely surround the opening to the optical sensor 40 between each pair of light shield layers 101 in order to completely block stray light from shining on the optical sensors. Reducing the stray light shining on a sensor may increase the contrast of the optical sensor 40 (i.e., the ratio between the amount of light illuminating the sensors with a particle 4 over the sensors and without a particle 4 over the sensor). This architecture can allow for the IC surface 7 to be relatively far away from optical sensors 40 (e.g., greater than 5 µm) without introducing significant stray light, which may be difficult to achieve without a light shield layer 101 and vias 102. By having a thick ILD above a sensor may reduce the light intensity incident on the optical sensors but may also allow for integration of more metal layers that may be used to perform various functions (e.g., carrying digital/analog signals, serving as power lines, concentration lines and/or separation wires).

As discussed above, for maximal detection signal-to-noise ratio, the optical sensor 40 may be smaller than the particle 4 such that the light from the light source 2 is fully attenuated. Alternatively, the sensor can be larger than the bead, but the opening in the light shield can be smaller such that the aperture is fully covered by the particle. Despite their reduced sensitivity, CMOS photodiodes may be superior to other photodetector implementations due to their high dynamic range (i.e. ability to detect a large range of light intensities). This large dynamic range can facilitate calibration of the intensity of the light source 2 to calibrate for the opacity of the sample for example.

The surface 7 of the IC 12 above the optical sensors may be composed of an interlayer dielectric (ILD) that is typical in CMOS processes and other commercial IC fabrication processes. This surface 7 may be composed of silicon oxide (e.g., LPCVD oxide, TEOS oxide), silicon nitride, silicon oxy-nitride, polyimide, or any other suitable material. The ILD can be modified prior to surface 7 coating (e.g., smoothened using chemical-mechanical processing, roughened and/or renewed using a wet etch, or combinations thereof). Prior to coating the surface 7 of the IC 12, an optically transparent material (e.g., evaporated silicon oxide, ITO, thin layer of metal, and any other material that may be coated and is at least partially optically transparent) can be deposited on the IC 12 to serve as an interfacial layer between the ILD material and the biological species used to functionalize the surface 7. The interfacial layer, as well as the rest of the ILD, need to be transparent or at least partially transparent to allow light to illuminate the optical sensors below. Having such an interfacial layer can allow the flexibility of using any material for surface 7 coating regardless of the actual ILD used in the fabrication of the IC, which may not be suitable for biological surface 7 coating itself. The silicon dioxide ILD layer can be coated with a hetero-bifunctional cross linker such as a silane linker to attach the desire chemical to the surface 7. The attachment link may be, for example, a biotin/streptavidin interaction that may be conjugate a capture species, such as a nucleic 12 acid, an antibody, or another protein to the surface 7 of the IC 12. Instead of an optically transparent surface 7 for coating, an opaque surface 7 (e.g., gold metal, carbon nanotubes, or combinations thereof) may be used and patterned into thin strips such that light may still pass between the strips and thus particles 4 binding to the surface 7 may still be detected.

Magnetic sensors (e.g., Hall effect sensors, magnetoresistive sensors, or combinations thereof) may be integrated onto the IC 12 in addition to the optical sensors described above. The magnetic sensors may be configured to measure the amount and/or distribution of magnetic material in the magnetic particles 81. The results of the measurement may be used in adjusting the separation and concentration forces and/or in changing the assay calibration parameters, as described above. Magnetic sensors may be used for other purposes, such as detecting magnetic particles 81, measuring and/or calibrating magnetic forces generated by other components of the system 10 (e.g., magnetic separation force generators, magnetic concentration force generators, external magnetic field forces such as a coil or a permanent magnetic). The magnetic sensors may also be configured in an array and may also be individually addressable. Magnetic sensors may be used to detect ambient magnetic fields; this information may be used to adjust the assay calibration parameters and/or to invalidate the assay results (e.g. when ambient magnetic fields are sufficiently strong to disrupt assay performance).

In a variation of the IC, the optical sensors can be replaced with magnetic sensors (i.e., the detection of particles 4, which must necessarily be magnetic particles 81, is performed by the magnetic sensors). However, CMOS optical sensors have several advantages over magnetic sensors. Optical sensors use less power than magnetic sensors (micro-amps versus milli-amps per sensor), can be readout more quickly (microseconds versus milliseconds per sensor) and can be more densely arrayed (arrays of millions versus tens of thousands). Moreover, the optical sensors can better control the protocol since they can detect the reagent sphere 3 re-hydrating by the change in the light reaching the surface 7 of the IC 12 and indirectly measure the viscosity of the sample.

FIG. 12 shows a top view and of the IC 12. Different regions of the chip (e.g., different trenches, different array banks, sections on the IC 12 spotted with a different receptor) can contain different concentrations or amounts of a particular receptor. For example, Assay Region 1 114 may be coated with the same receptor as first assay region 115 and second assay region 116, but may contain only 10% or some other predetermined percentage of the receptor surface concentration of first assay region 115. Likewise, first assay region 115 may contain only 10% or some other predetermined percentage of the receptor surface concentration of second assay region 116. By having different amounts of each receptor in different regions of the chip may result in: (1) broader detection dynamic range by ensuring a receptor concentration exists that does not result in signal saturation or too low of a signal (i.e., too few if any bound particles 4), (2) error checking functions by cross-checking each receptor concentration to make sure a signal is consistent, and (3)

providing the ability to perform quantitative controls. Assay regions having different target analytes and/or different concentrations of a particular receptor to a single target analyte may be coated in common centroid fashion (i.e., all sets of regions with the same characteristic have a common center or approximately common center on the surface 7 of the IC 12).

FIG. 12 shows that different regions of the chip (e.g., different trenches, different array banks, sections on the IC 12 spotted with a different drop) can contain different concentrations or amounts of a particular receptor. Negative control regions are defined as regions where target analyte cannot be detected, independent of the actual concentration of the target analyte in the aqueous sample. For example, negative control regions (i.e., first negative control region 117 and second negative control region 118) may not be coated with a receptor to the target analyte. As a result, particles 4 will not bind to the surface 7 in the negative control region. As discussed above negative controls may be achieved by a prevention chemical instead to ensure that no binding occurs. Negative controls may be used to ensure that particles 4 are introduced over the surface 7 in the negative control region (i.e., this checks that particles 4 exist and that they have a proper surface concentration range). Factors such as improper or old reagents, poor environmental conditions, and misuse by the user may cause particles 4 to bind even though no target analyte is present. Having negative controls ensures that the reagents present in the system 10 and environmental conditions of the surroundings (e.g. temperature) allow for regions with no target analyte to exhibit no specific binding or strong non-specific binding. Positive controls regions (i.e., first positive control region 110, second positive control region 111, third positive control region 112, and fourth positive control region 113) are defined as regions where the particles 4 can bind specifically, regardless of the concentration of the target analyte in the aqueous sample. For example, positive control regions or positive control sample chambers may contain dried and bound target analyte or any other sort of target analyte or another molecule that mirrors a target analyte such that binding events occur (i.e., particles 4 bind to the surface 7). Factors such as improper or old reagents, poor environmental conditions, and misuse by the user, may hinder specific binding. Thus, having positive controls can ensure that the reagents present in the system 10 and environmental conditions of the surroundings (e.g. temperature) allow for successful binding to take place. Both negative controls and positive controls may be used to detect and compensate and/or correct for environmental variations (e.g., temperature, mechanical stress, light level, orientation of the system 10, and other sources of variations). Negative and positive controls may be used to dynamically modify the assay calibration parameters and other modifiable parameters on the chip (e.g., various magnetic forces, assay time, or combinations thereof). Controls can be performed concurrently with the assay.

FIG. 12 shows that one or more of the positive control regions (i.e., first positive control region 110, second positive control region 111, third positive control region 112, and fifth positive control region 114) can be controls that correspond to a particular concentration of target analyte (i.e., between negative and positive). This may be implemented, for example, by having different amounts of dried and bound target analyte in each region or by having a different amount of receptors that bind to the target analyte. For example, first positive control region 110 may contain a high concentration of dried and bound target analyte on the surface 7 or optionally in a chamber separating first positive control region 110 from other regions, whereas second positive control region 111 may contain a smaller predetermined percentage of the dried or lyophilized target analyte (e.g., 10% of the amount for first positive control region 110). Third positive control region 112 and fifth positive control region 114 may contain different amounts of lyophilized target analyte as well. By having several levels of controls, one may more accurately determine the assay calibration parameters as the assay progresses than when using just negative and positive controls, and thus one may more accurately compensate the reading for environmental changes, reagent variations, and user misuse, that may contribute to changing the signal level. The positive controls that ensure binding can also be used to measure the binding forces of the specific interaction by applying a know force on the magnetic particles 81.

In a variation of the system 10, all or a portion of particles 4 in the SPDM 8 may be pre-coated with the target analyte and thus may always specifically bind to the surface 7 of the IC 12. This may be effectively another way of implementing positive controls that can ensure that the reagents present in the system 10 and environmental conditions of the surroundings (e.g. temperature) allow for successful binding to take place.

The use of integrated circuit 12 technology can enable scaling the number of sensor to a high density or quantity of sensors, such as over a thousand or over a million individual sensors, or a low density or quantity of sensors (e.g., 10-100 sensors). A high number of small sensors can provide large detection areas while each sensor still retains high sensitivity to small particles 4 (i.e., only small sensors can detect small particles 4 with high fidelity in a practical amount of time). Such characteristics cannot be achieved with a few large sensors as large sensors would not be sensitive enough to detect small particles 4. Having a high density of sensors over large detection areas, one IC 12 may contain several regions for detecting multiple analytes and having multiple control levels, with each region being of sufficient size to obtain accurate target analyte concentration readout.

The optical sensors may be configured to detect particles 4 in real time, prior to the particles 4 actually coming in contact with the surface 7 of the IC 12. For example, an optical sensor 40 may sample the light intensity at very short intervals (e.g., once every 1 ms) and therefore may be able to detect a particle 4 that is approaching and about to land on the surface 7 (e.g., when the particle 4 is several micrometers away from the surface 7). In this way, the optical sensors may be used to measure the sedimentation velocity of the particles 4 and therefore provide information about the properties of the particles 4 (e.g., surface 7 roughness, size, density, weight) and/or the properties of the aqueous sample (e.g., viscosity, flow). As discussed above, these parameters may be used in adjusting the assay calibration parameters and other parameters to further improve the accuracy of the assay. In general, optical sensors may detect particles 4 within 1-20 um of contact with the surface 7, depending on the particle 4 size.

The optical sensors may be configured to detect particles 4 that are nanometer sized (e.g., between 5 nm to 500 nm in diameter). Nanometer-sized particles 4 (also referred to as nanoparticles) may be used to measure the binding kinetics of a target analyte. This can be done, for example, by measuring the light intensity of the optical sensors at short time intervals (e.g., every few milliseconds to every few seconds) to determine how quickly the nanoparticles settle and bind to the surface 7 of the IC 12. Binding kinetics may be represented by parameters associated with the rate of binding, and unbinding of the bonds between target analytes and receptors (e.g., rate constants, activation energies, association constants, dissociation constants, equilibrium levels, and other parameters). The control module or an external computing device may be used to calculate the binding kinetics parameters from the measurements obtained by the optical sensors. Even if an optical sensor 40 is not capable of detecting a single nanoparticle, an array of optical sensors or one optical sensor 40 may be able to detect several (e.g., tens to thousands) nanoparticles, thereby still providing an estimation of the binding kinetics of that particular target analyte. Binding kinetics may be useful for assay characterization, drug discovery, and many other applications and may be used in modifying the assay calibration parameters. External magnets (e.g., coils integrated onto the PCB 9) or on-chip electromagnets (e.g., concentration conductors 80) may be used to pull the magnetic nanoparticles towards the surface 7 to speed up binding kinetics and to pull them away from the surface 7 to perform separation. The nanoparticles used do not necessarily need to be magnetic in order to measure the binding kinetics; the nanoparticles simply need to modulate the light intensity hitting the sensor (e.g., by being fully or partially opaque or by reflecting, refracting, or dispersing the light). Using optical sensors for measuring binding kinetics, as opposed to magnetic sensors, is generally a preferred method as it allows using non-magnetic particles. Further, magnetic sensors require that magnetic particles 81 be polarized prior to detection, which is difficult to perform without imparting significant magnetic forces on the magnetic particles 81 and thus distorting kinetic measurements. Neither the optical sensors 40 nor the light source 2 impart significant forces on the particles 4 and thus kinetic measurements are undistorted.

The system 10 can be configured to permit variation of the environmental conditions between multiple sensing areas. Environmental conditions may include temperature, viscosity, pH, and other physical, chemical, and biological parameters. One or more heating elements and thermometers may be incorporated into the surface 7 such that they permit localized temperature control within one or more sensing areas. Electrodes may be placed in or in the vicinity of optical sensing areas 41 and may be used to modify the pH and/or ion concentration of the aqueous sample 5 in the optical sensing areas 41 by placing a potential difference between the electrodes. By simultaneously performing multiple assays while varying environmental conditions, assay specificity may be improved, and the influence of external environmental parameters can be reduced.

Different ensembles of particles 4 can be colored with dyes or metal nanoparticles. Ensembles of particles 4 of different color can be coated with different chemicals and/or different concentrations of the same chemical in order to perform multiple assays concurrently. The optical sensors 40 in the IC 12 can detect the different colors that can correspond to different target analytes or different concentrations of the same analyte. As discussed above, different types of photodiodes or bayer color filters can also be used to detect the different colors.

Different ensembles of particles 4 can be darker. Optical sensors 40 in the IC 12 can measure the amount of light and determine the type of particle. Using these approaches, multiplexed assays and assays with comprehensive assay controls can be performed by the same IC 12 in the same sedimentation capillary 13.

Figure 13A:
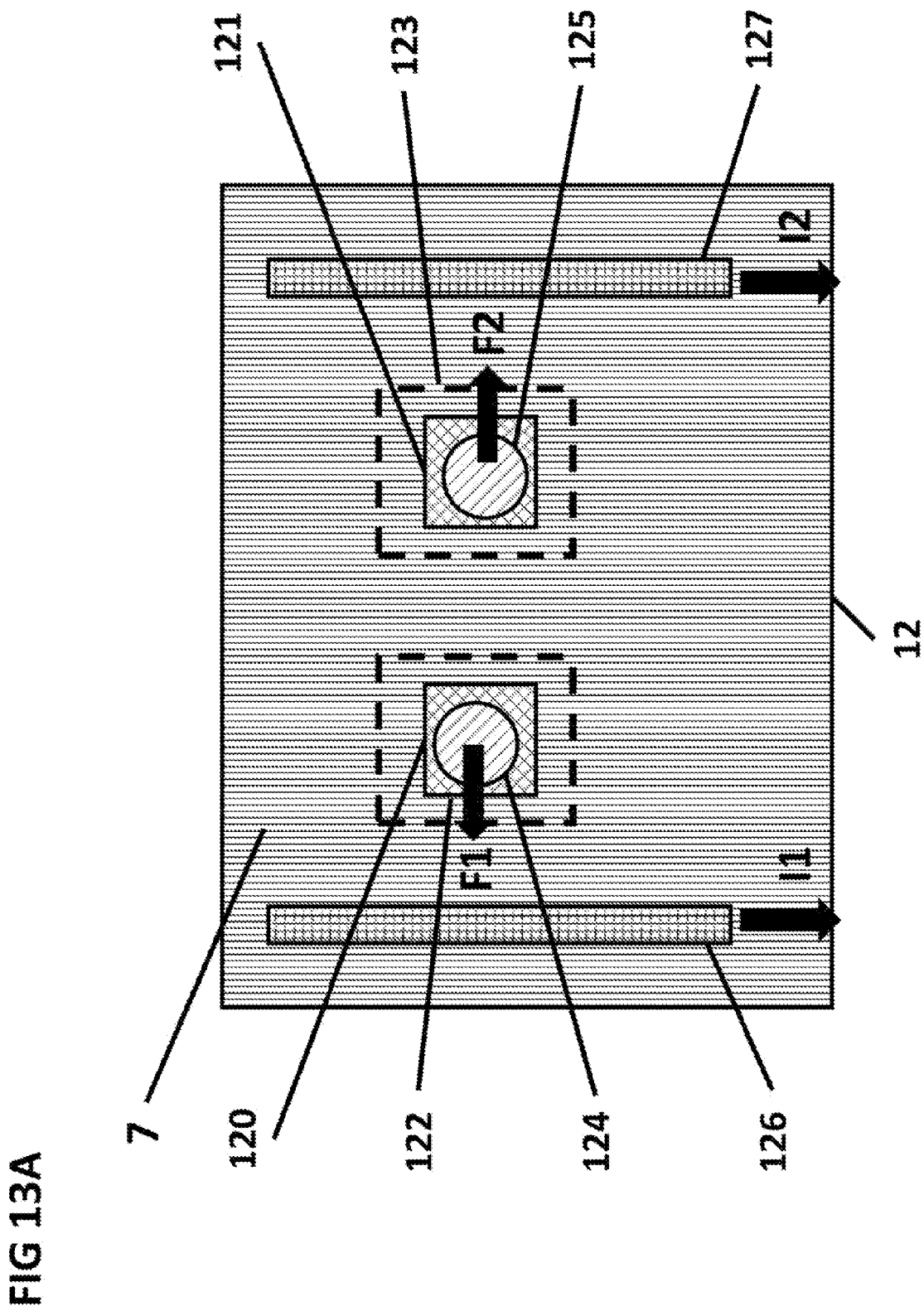
FIGS. 13A and 13B show a top and cross sectional side view, respectively, of a variation of the IC 12 adapted to generate multiple forces, F1 and F2, on magnetic particle 124 and magnetic particle 125, respectively.
Figure 13B:
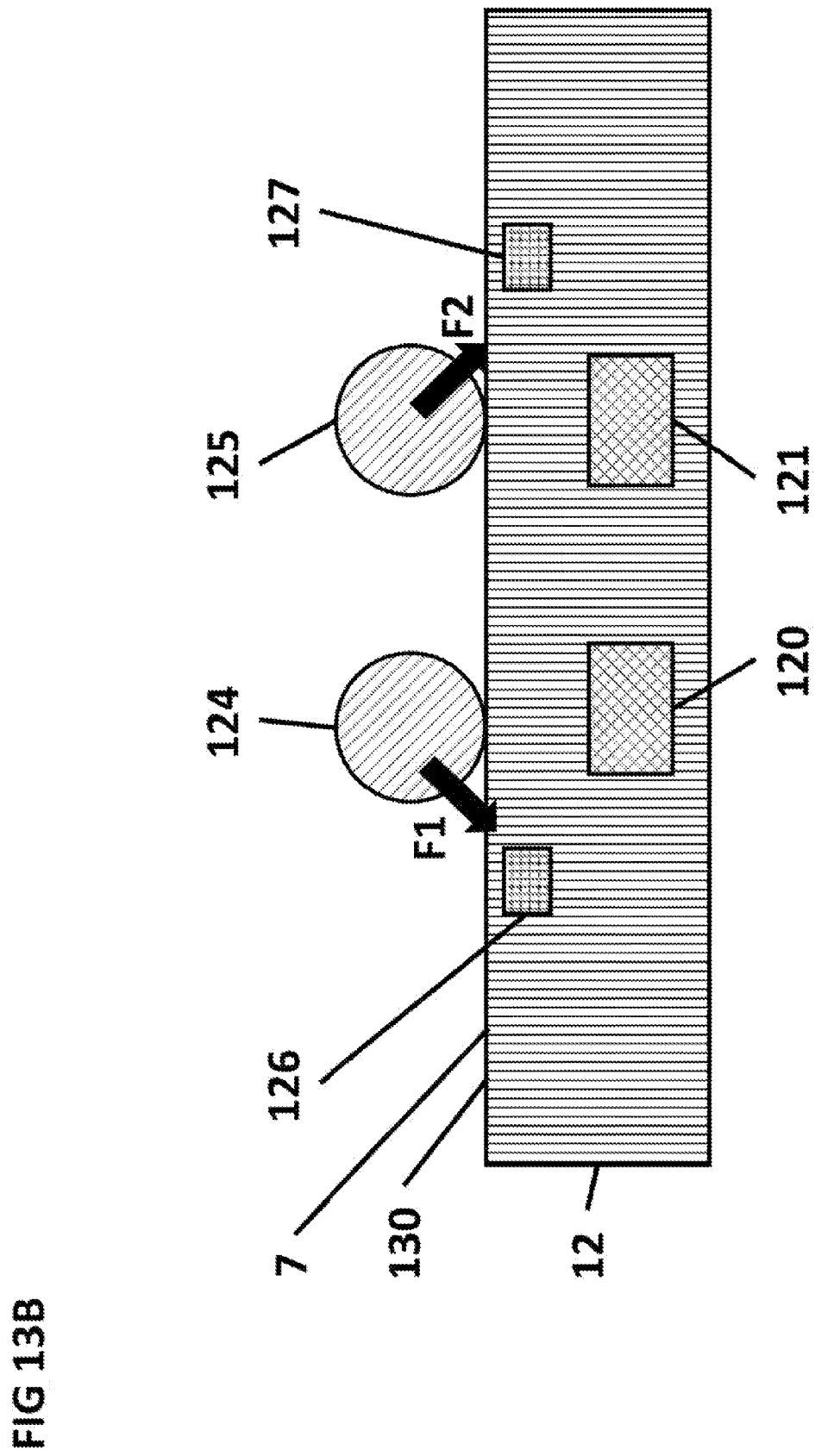

FIGS. 13A and 13B show a top and cross-sectional side view respectively of a portion of an integrated circuit 12 with two magnetic particles on its surface 7.

FIG. 13A shows a current I1 passing through separation conductor 126. The current I1 can generate a magnetic field that pulls magnetic particle 124 with a magnetic force F1. The vector of the force F1 points in the direction of the separation conductor 126. The current I1 can be ramped at arbitrary rate or modulated in amplitude and frequency at arbitrary rate. Different force ramps can provide information on the affinity of the bond. A current I2 of different intensity can pass through separation conductor 127 simultaneously, resulting in a magnetic field generating a magnetic force F2 on the magnetic particle 125.

Figure 14A:
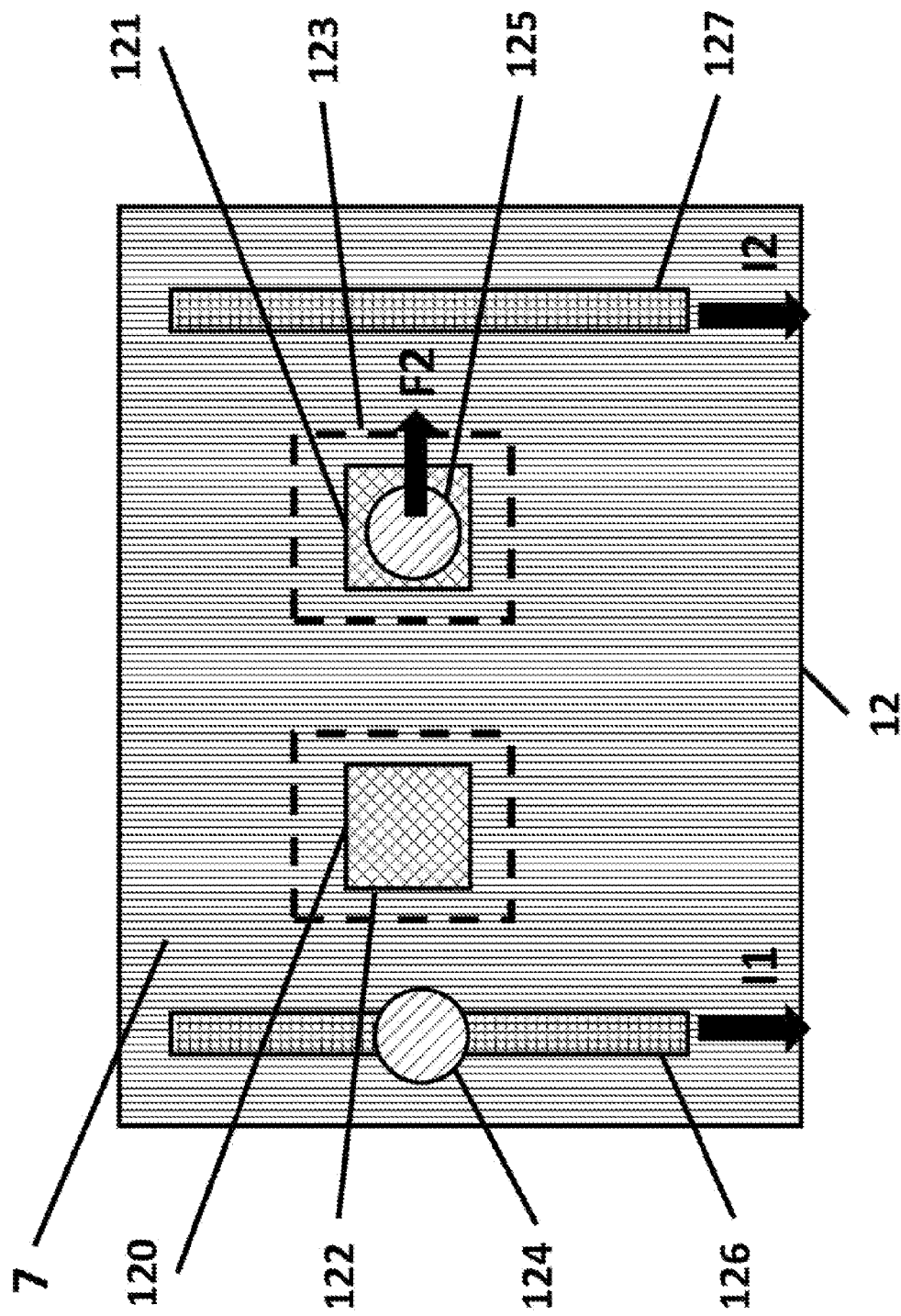
FIGS. 14A and 14B show a top and cross sectional side view, respectively, a scenario presented in FIGS. 13A and 13B where the first force F1 can be strong enough to displace magnetic particle 124 from atop the first magnetic particle sensor 122, while the second force F2 can be weak enough to leave the second magnetic particle 125 immobilized atop the second magnetic particles 81 sensor 121.
Figure 14B:
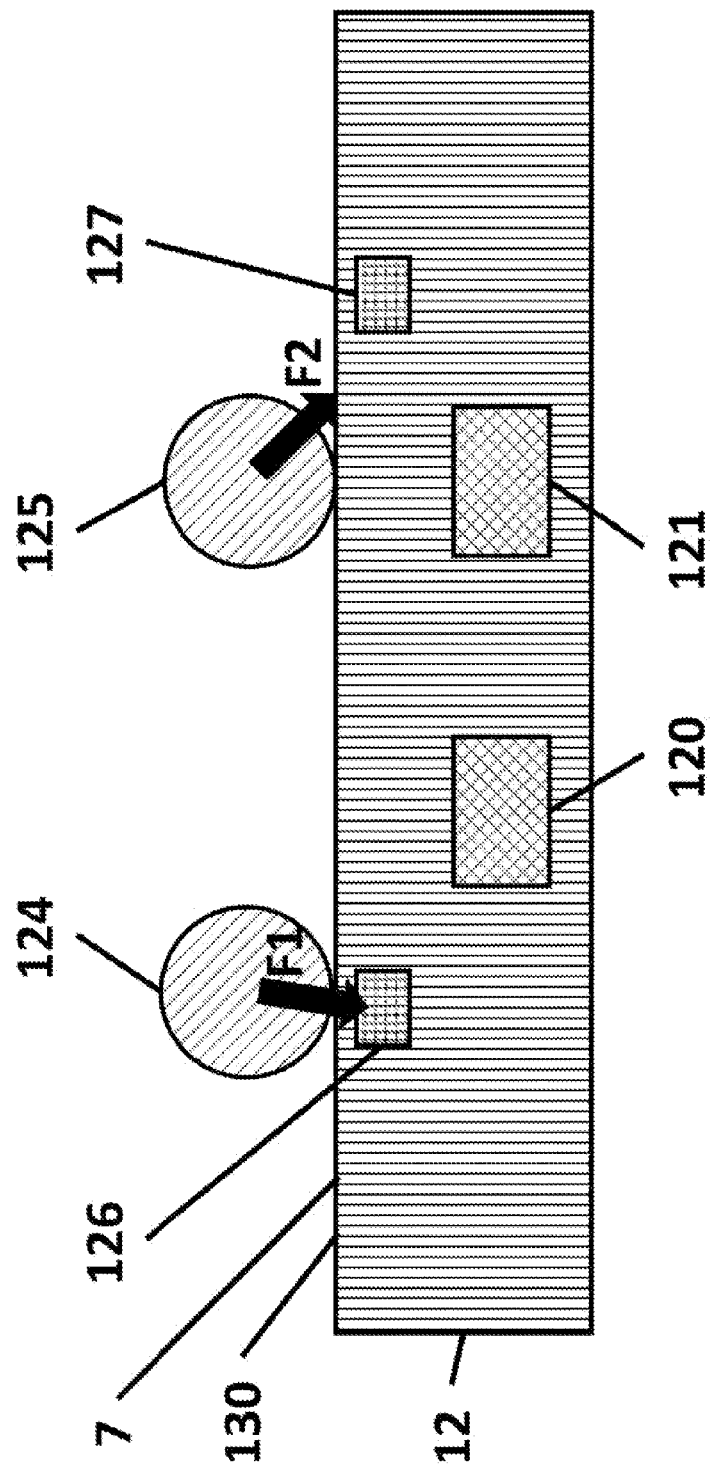

FIGS. 14A and 14B show a top and cross-sectional side view respectively of a portion of an integrated circuit 12 with two magnetic particles on its surface 7. Force F1 can be strong enough to displace magnetic particle 124 from atop optical sensor 120, but force F2 can be weak enough to leave magnetic particle 125 immobilized atop optical particles 121.

Biological samples can have variations (e.g., in pH and ionIC 12 strength) that can affect the strengths of the specific and non-specific bonds. These variations cannot be known a priori, so magnetic forces may need to be dynamically tailored to the sample for accurate detection of one or more target analytes. To do so, the strengths of the specific and non-specific bonds can be measured prior to performing the assay and the magnetic forces used for separation may be adjusted accordingly. To measure the strength of the non-specific or specific bonds, magnetic fields of increasing strengths may be generated by passing current of increasing intensities through the magnetic separation field generators and measuring, at each time instant, the amount, concentration, proportion, or ratio of magnetic particles 81 removed from an optical sensing area 41 or remaining on an optical sensing area 4. The strength of the non-specific bonds may correspond to the smallest magnetic field of the series of increasing magnetic fields that removes a predetermined portion (e.g., one half) of the non-specific bound magnetic particles 81 from the optical sensor areas 41. To ensure that only non-specific bonds are measured, optical sensor areas 41 may be coated with a prevention chemical that may prevent a binding with the surface 7 of the magnetic particles 81, such as casein or albumin. To ensure that only specific bonds will be measured, the sensor areas 41 may be coated with an activation chemical that may ensure binding with the surface 7 of the magnetic particles 81 61, such as one or more of the target analytes.

Statistical analyses can be performed (e.g., by extracting peaks from a histogram of forces that remove a certain amount or percentage of particles 4) to determine what the non-specific binding forces and specific binding forces are. Several other parameters may be varied, such as the rate of the increase of the magnetic separation force or the amount of time each magnetic force is applied, that may provide more information on the binding forces and may be used to adjust the amplitude, rate, and time of magnetic separation forces while performing an assay. The measurement of the specific and non-specific bonds may be performed simultaneously on-chip by multiplexing. An assay may be performed concurrently with the specific and non-specific bond measurements, and the results from the specific and non-specific bond measurements may be used to interpret the results (e.g., adjust the assay calibration parameters). The specific and non-specific bond measurements results may be used to calibrate the magnetic forces in a subsequent assay.

This subsequent assay may be performed on the same integrated circuit 12, but subsequently to the specific and non-specific bond measurements. The specific and non-specific bond measurements results may be retrieved in real-time and used to calibrate the magnetic forces in a concurrent assay. This concurrent assay may be performed on the same integrated circuit 12 or on another integrated circuit 12.

The use of a range of magnetic separation forces can be used to increase the dynamic range of the assay. Different separation conductors 60 can produce different forces on the magnetic particles 81 in order to discriminate between the particles 4 with few specific interactions (e.g. 1-10) and many specific interactions (e.g. 10-100). In this manner, low and high concentration of the target analyte can be quantified using the same IC 12 at the same time without saturating the optical sensors 40 with many specifically bound magnetic particles 81 or removing all the magnetic particles 81 into the separation region 70. The use of a range of magnetic separation forces can be used to independently optimize multiple assays run concurrently on the same IC 12. The different reagents needed to perform multiple assays react differently to different sample matrixes. By using different forces, the separation forces for each assay can be independently calibrated for optimal performance.

FIG. 15 shows a cross-section side view of the system 10 with dried reagent 150 throughout the delivery capillary 14 and the sedimentation capillary 13. The dried reagent 150 inside the delivery capillary 14 and sedimentation capillary 13 can promote wicking of the aqueous sample 5 by absorbing and dissolving in the aqueous sample 5 and thus promoting sample transport through the system 10. The dried reagents 150 can be dried or lyophilized; they can be inert ingredients (such as polyethylene glycol) or may be functionalized by including, anti-coagulation agents or other suitable reagents. The dried reagents 150 may incorporate thickening or other viscosity control agents. The reagents may be homogenous or heterogeneous: for example, layers of slowly-dissolving inert material may be placed between layers of active reagents to ensure sufficient reaction time. The capillaries can be manufactured from a transparent material, for example plastic, glass, or a combination thereof, to transmit light to the surface 7 of the IC 12. The sedimentation capillary 13 and the delivery capillary 14 can be made of a flexible material to allow for a tight seal to the surface 7 of the IC 12 by compression from above. A gasket can also be used to seal the interface between the bottom of the capillaries and the surface 7 of the IC. The bottom of the capillaries can also be placed above the surface 7 of the IC 12 by a distance less than 5 mm and gravity can ensure that the aqueous sample 5 is wicked onto the surface 7 of the IC 12. Multiple delivery capillaries can lead to multiple sedimentation capillaries that hold different reagent spheres 3. These sedimentation capillaries can be over different areas of the same IC or different ICs.

FIG. 16A and FIG. 16B are cross-section side views of the top inlet to the delivery capillary 14. In FIG. 16A, dried reagents 150 are located in proximity to the filter 6 with an air gap 151 separating them (which may be a result of manufacturing tolerances). In FIG. 16B the dried reagents 150 are placed in direct contact with the filter 6. The dried reagents 150 accelerate the transfer of aqueous sample 5 through the filter 6 material by absorbing and dissolving in the sample fluid. The dried reagents 150 can promote the wicking of fluid from the input port to the delivery capillary 14, which can otherwise be obstructed by surface 7 tension effects.

Figure 17:
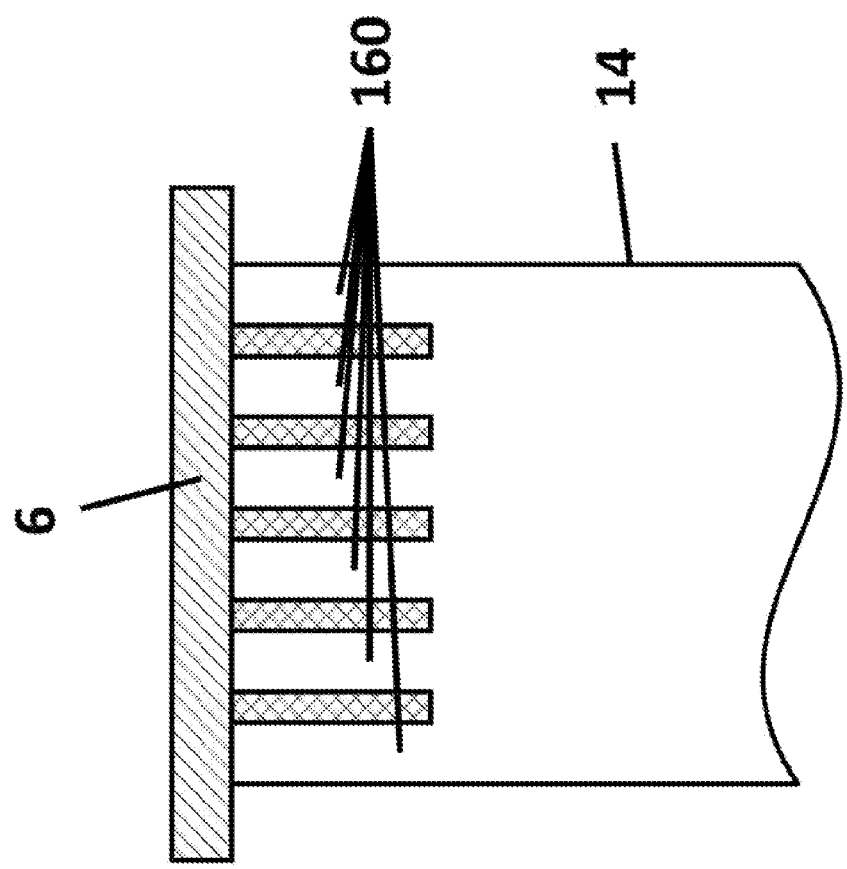
FIG. 17 is a cross sectional side view of a variation of the inlet of the delivery capillary 14 with wicking capillaries 160.

FIG. 17 is a cross-section side view of another version of the inlet to the delivery capillary 14. Wicking capillaries 160 of smaller diameter than the delivery capillary 14 can be placed in proximity to the filter 6. The wicking capillaries 160 can accelerate the transfer of the aqueous sample 5 through the filter 6 material. The wicking capillaries 160 may have a constant diameter, or may be tapered in a way to promote the flow of the aqueous sample 5. The wicking capillaries 160 can be manufactured using injection molding, micro-injection molding, extrusion or micro-fabrication. The wicking capillaries can be from 10 μm to 10 mm wide and from 10 μm to 10 mm long.

Figure 18:
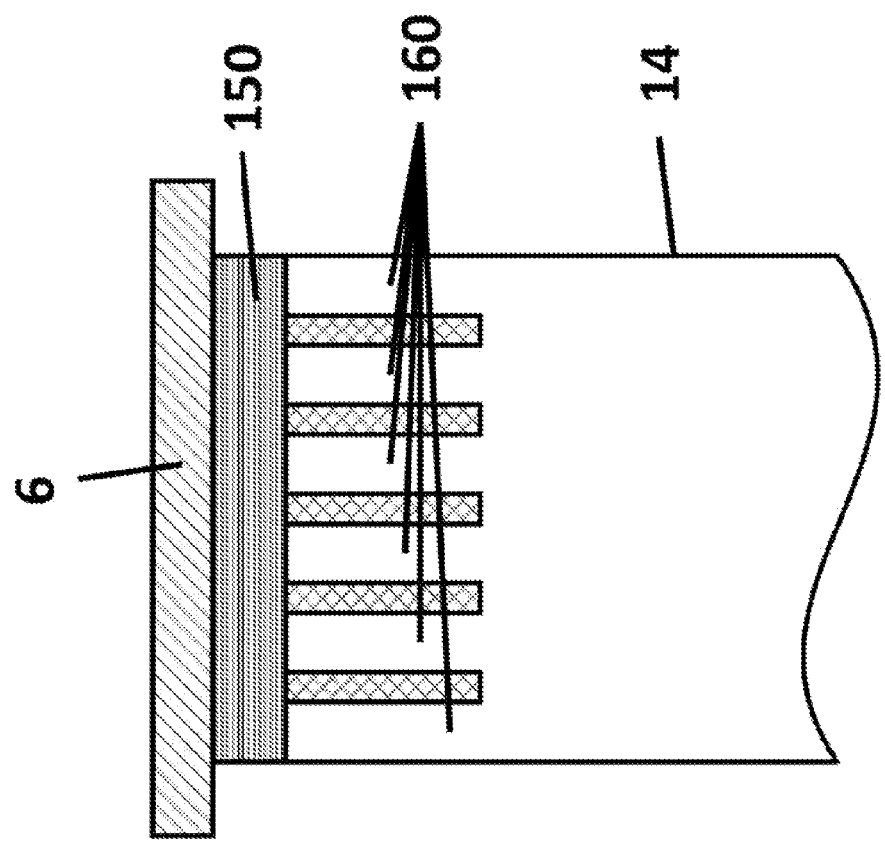
FIG. 18 is a cross sectional side view of a variation of the inlet of the delivery capillary 14 with dried reagents and wicking capillaries 160.

FIG. 18 is a cross-section side view of another version of the inlet to the delivery capillary 14. A layer of dried reagents 150 is placed between the filter 6 and the wicking capillaries 160. The dried reagents 150 dissolve and promote the transfer of aqueous sample 5 through the filter 6 material, and the wicking capillaries 160 assist with wicking the fluid into the delivery capillary 14, which may be of a larger diameter.

Figure 19:
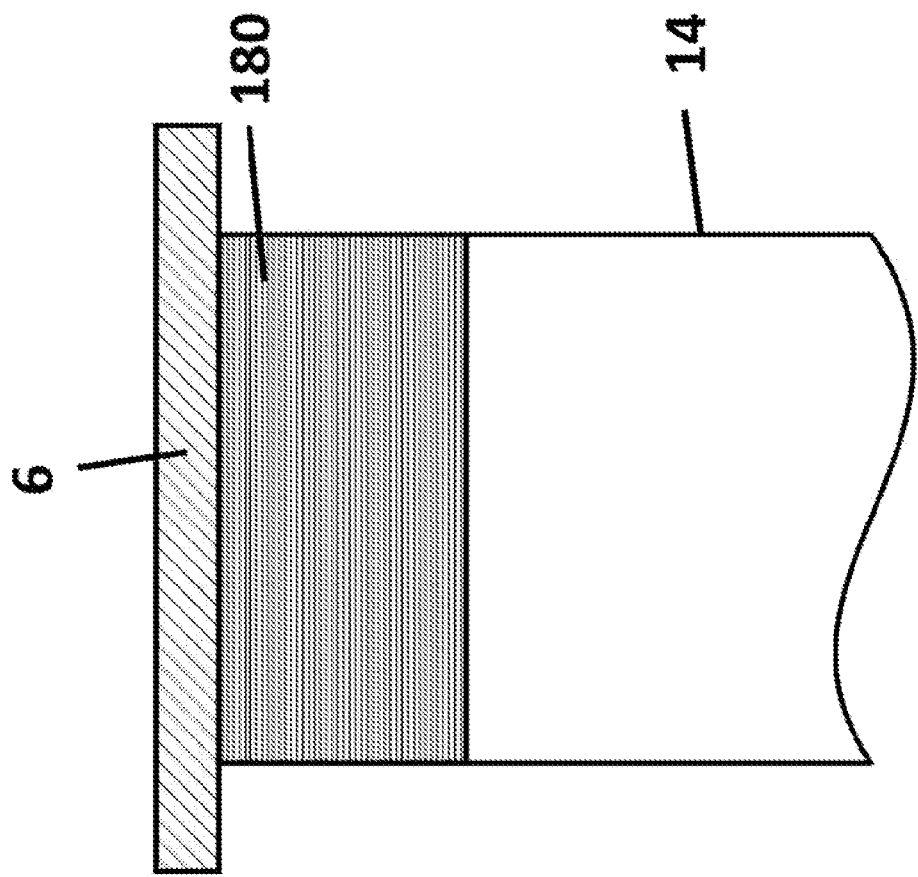
FIG. 19 is a cross sectional side view of a variation of the inlet of the delivery capillary 14 with a porous material 180.

FIG. 19 is a cross-section side view of a variation of the inlet to the delivery capillary 14. A layer of porous material 180 can be placed between the filter 6 and the delivery capillary 14. The porous material 180 can promote the transfer of the aqueous sample 5 through the filter 6 material by absorbing the fluid. The porous material 180 can be glass fiber, synthetic fibers or other porous materials with pore sizes from 0.1 μm to 100 μm.

Figure 20:
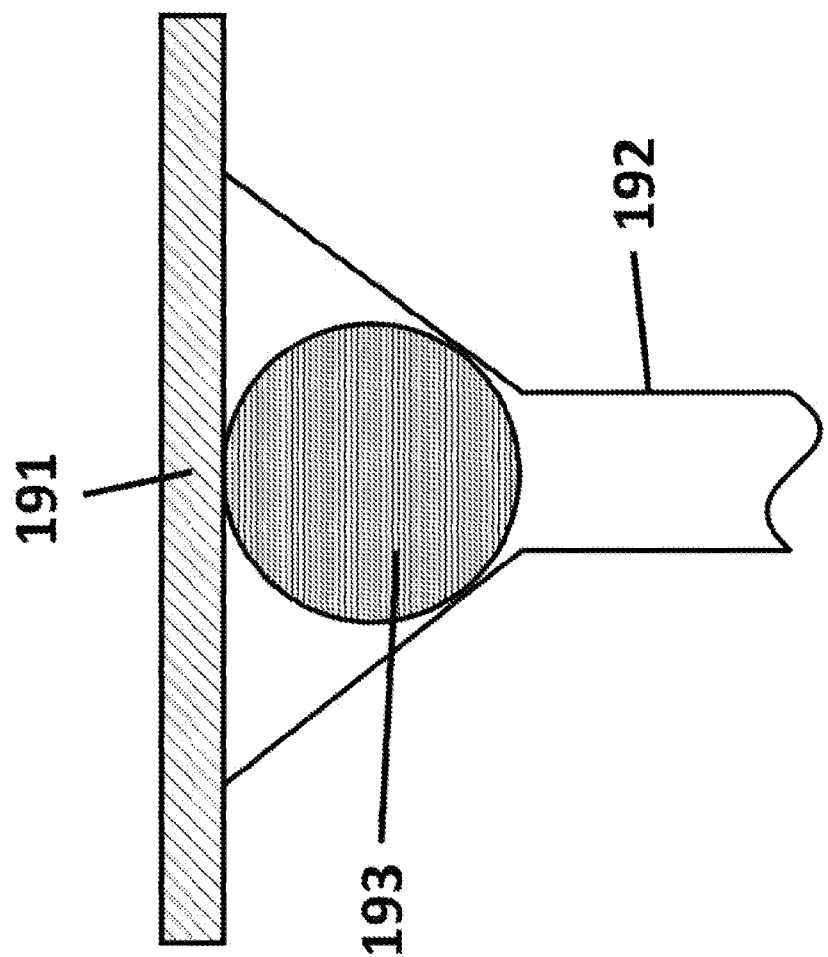
FIG. 20 is a cross sectional side view of a variation of the system 10 including a reagent sphere 3 placed into a tapered section at the top of the sedimentation capillary 193.

FIG. 20 is a cross-section side view of a variation of the top of a capillary 192. A spherically-shaped reagent sphere 193 is placed into a tapered opening at the top of the capillary 192. A cover layer 191 can be placed over the opening to keep the reagent sphere 193 stationary. After the placement of the reagent sphere 193, the cover layer 191 can be attached to the capillary 192 using a ring of double sided tape. This variation may form the inlet of the sedimentation capillary 13, where the cover layer may be a gas-permeable seal to let air escape but keep the reagent sphere 3 stationary. The reagent sphere 3 can be manufactured by lyophilization with constant agitation of the dispense fluid to ensure homogeneous dispersion of the particles 4 in suspension prior to dispensation into the liquid nitrogen. This variation may also form the inlet to the delivery capillary 14, where the cover layer 191 may be the filter 6, and the reagent sphere 193 may act to promote the flow of reagents into the delivery capillary 14. Advantages of this structure include a simple manufacturing process: the reagent sphere 193 may simply be pick-and-placed into the inlet, and the cover layer placed on top. Because of the conical geometry, the structure can tolerate significant variation in the diameter of the reagent sphere 193, for example if the cover layer 191 is made of a flexible material. Recognizable colored dies can be introduced in the reagent spheres 193 to aid in the rapid quality inspection of the system 10, i.e. to quickly ensure that the correct reagent sphere 193 has been deposited at the top of the appropriate capillary 192.

Figure 21:
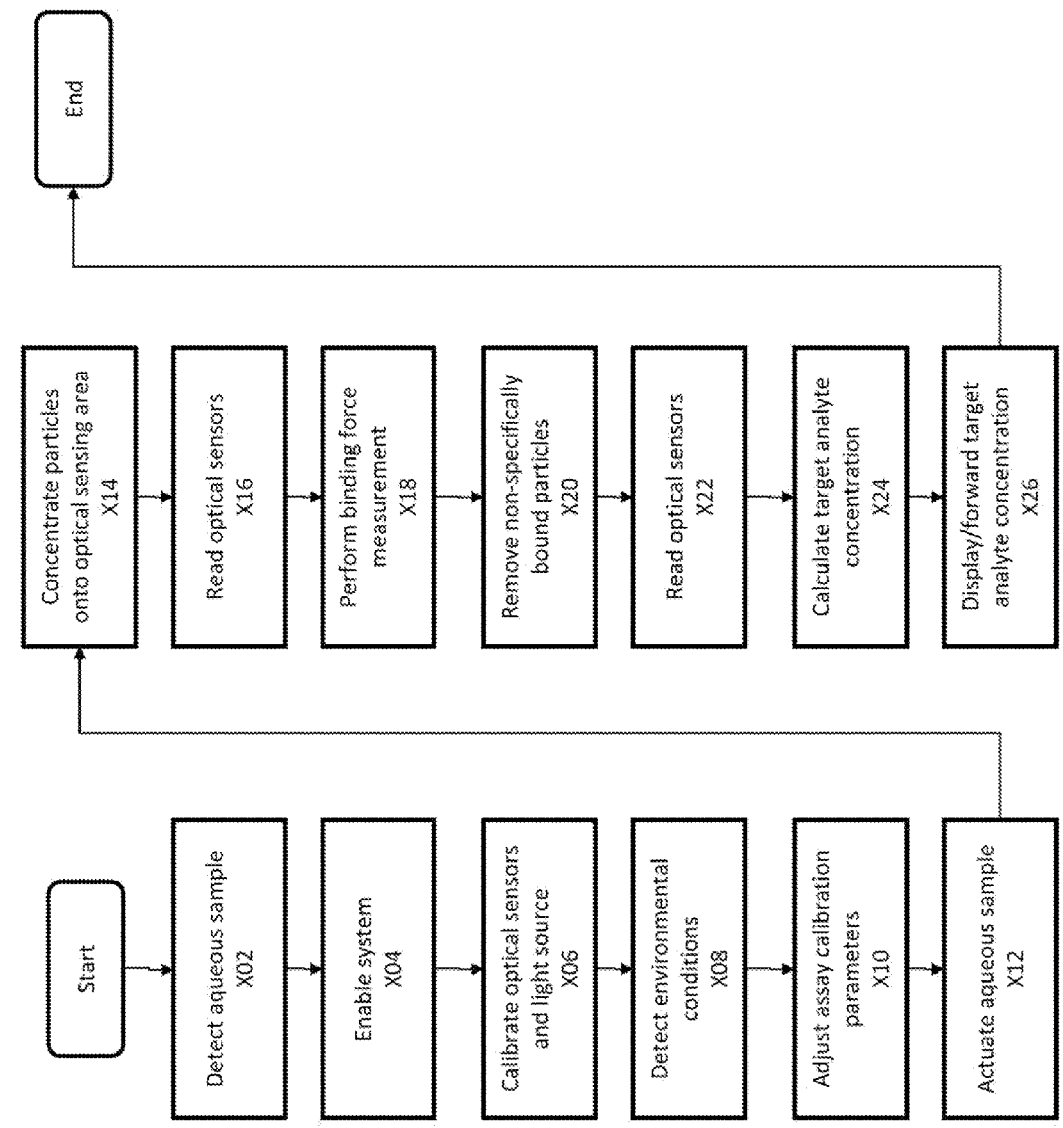
FIG. 21 is a variation of a method performed by the system 10.

FIG. 21 shows a flowchart of a process that can be an assay performed by a particle detection system to quantify the concentration of a target analyte. The process shown in FIG. 21 may be implemented using one or more components of the particle detection system. The sequence of the method shown in FIG. 21 may differ among variations, and that one or more elements of the method shown in FIG. 21 may be repeated, replaced, and/or omitted. Further, additional steps may be added in between any of the steps shown in FIG. 21.

In STEP 212, a user introduces an aqueous sample 5 (e.g., a finger stick of blood, a fluid from a pipette, or combinations thereof) onto a membrane filter 6 of the system 10, which may be filtered by a filter 6, transported onto the surface 7 of the IC 12, and detected by one or more sensors of the system 10. As discussed above, the membrane filter 6 may remove particulate matter (e.g., red blood cells, white blood cells, other cells and micron size particulates). Subsequently, the aqueous sample 5 may flow through a capillary over a sensor that is able to detect the presence of the aqueous sample 5. The sensors detecting the fluid may be moisture sensors (e.g., electrodes, optical sensors) on the IC 12 or elsewhere in the system 10, touch sensors near the membrane filter 6 or elsewhere on the device, temperature sensors, and any other elements for detecting the presence of the aqueous sample 5. The moisture sensors can be omitted and/or no detection of the aqueous sample 5 takes place (i.e., STEP 212 may be omitted). After STEP 212, the process proceeds to STEP 214.

In STEP 214, one or more components of the system 10 are enabled in response to detecting the presence of the aqueous analyte. For example, sensors detecting the presence of the aqueous sample 5 may send a signal to a control module, which changes state (e.g., switches from an idle state to an active state). Alternatively, the signal from sensors detecting the presence of the aqueous sample 5 may be directly sent to other components of the system 10 to enable or calibrate these components. Still alternatively, a user or an operator of the system 10 enables the system 10 (e.g., with a button, a touch, a voice input, and any other input) which then triggers a change of state in the control module. Prior to enabling other components of the system 10 in STEPS 216-232, the control module can enable subcomponents of the control module itself or other auxiliary components (e.g., enable memory banks, enable respective accessory circuitry, enable PCB 9 components such as voltage regulators, amplifiers, ADCs, and other components standard in the art). By keeping most components in an off-state and running at low speed, the control module can save battery power, for example allowing the device to stay in an idle state for a long time (e.g., months to years). In addition to enabling various components, the control module may perform certain initialization procedures (e.g., check status of all components, run internal and external error checking routines, and other procedures) prior to enabling other components of the system 10 in STEPS 216-232. After STEP 214, the process proceeds to STEP 216.

In STEP 216, the light source 2 and the optical sensors 40 may be calibrated. This step may be performed prior to any of the particles 4 sedimenting on the surface 7 of the IC 12, and may be performed either prior to or after the dissolution of the reagent sphere 3 containing the particles 4. If either the light source 2 is too strong/weak or the optical sensors 40 are too sensitive/insensitive, a positive signal (i.e., a particle sedimenting over an optical sensor 40) and a negative signal (i.e., a particle not sedimenting over an optical sensor 40) may be difficult to differentiate, and thus a calibration step may be necessary. The light source 2 intensity or duration may be varied until the signal from optical sensors reaches a certain level (e.g., half of the optical sensor 40 saturation value), and then the time and/or intensity may be stored in memory and used later during actual particle detection. Alternatively, the intensity and time the light source 2 is on may stay constant and the sensitivity of the optical sensor 40 may instead be modulated (e.g., by changing the bias voltage). A combination of these two calibration techniques may be used or that any other calibration technique may be used, for example, to ensure that the difference between the signal generated by an optical sensor 40 with a particle 4 over it and an optical sensor 40 without a particle has a high signal to noise ratio (i.e., can be readily quantified). Calibration may be not necessary and STEP 216 may be omitted. After STEP 216, the process proceeds to STEP 218.

In STEP 218, various environmental conditions may be detected and optionally stored in a memory. For example, the orientation, acceleration, velocity, or any other physical parameter of the system 10 may be detected and measured by one or more inertial sensors and stored in memory. In another example, the temperature of the surroundings and/or of the aqueous sample may be detected by one or more temperature sensors and may be stored for later use. In yet another example, the viscosity of the aqueous sample may be measured by one or more viscosity sensors and may be stored in memory. Many other parameters exist that may modify assay performance (e.g., humidity, time of day, particle variations, and others) may also be measured and stored in a memory. The measurements in STEP 218 may be performed preceding, (continuously or discontinuously) concurrent with, or subsequent to the assay. Measurement of environmental conditions may not be necessary and STEP 218 may be omitted. After STEP 218, the process proceeds to STEP 220.

In STEP 220, assay calibration parameters may be adjusted based on the measurement results from any of the prior steps (e.g., temperature reading, viscosity of aqueous sample, or combinations thereof). As discussed above, assay calibration parameters may include a standard curve, assay time, magnetic separation force and concentration force amplitude and duration, and any other parameters that can modify the amount of beads binding, the amount of beads removed, the function from amount of beads to target concentration (e.g., standard curve), and any other assay parameter. The adjustment of assay calibration parameters in STEP X08 may be performed not only prior to the assay, but during the assay, after the assay, and continuously throughout the assay (e.g., temperature, viscosity, and any other parameters may be monitored throughout the duration of the assay and be used in changing the assay calibration parameters). The assay calibration parameters may be stored in memory and the assay result (e.g., particle number) may be compared to the assay parameters and/or modified according to the assay calibration parameters to yield the final assay result. Adjustment of assay calibration parameters may not be necessary and STEP 220 may be omitted. After STEP 220, the process proceeds to STEP 222.

In STEP 222, the aqueous sample 5 and/or the entire system 10 may be actuated. Actuation may be performed by using a vibrator module to vibrate the entire system 10, by using magnetic field generators (e.g., external coils) to move magnetic particles 81 about the aqueous sample. As discussed above, actuation of the aqueous sample 5 may speed up assay kinetics and reduce the required assay time. The intensity, frequency, direction, and/or duration of the actuation may be dependent on the measurements performed in STEPS 216 and 218. Actuation of the aqueous sample 5 may not be necessary and STEP 222 may be omitted. After STEP 222, the process proceeds to STEP 224.

In STEP 224, the particles 4 may be concentrated into one or more optical sensing areas 41 on the IC 12. By now the aqueous sample 5 may have dissolved or partially dissolved the reagent sphere 3 and particles/reagents may have been released and allowed to mix with the target analyte in the aqueous sample 5 and may be sedimenting on the surface 7 of the IC 12. As described above, the control module may enable, either in parallel or in series, any magnetic field concentrators integrated on the IC 12 or positioned elsewhere in the system 10 to allow the particles 4 to sediment more quickly to the IC 12 surface 7 and/or to direct the particles 4 to the one or more optical sensing areas 41 on the IC 12 surface 7. The particles 4 may sediment via gravity randomly on the surface 7 and the concentration step may be unnecessary (i.e., STEP 224 may be omitted). After STEP 224, the process proceeds to STEP 226.

In STEP 226, optical sensors 40, whether in assay regions or control regions, may be read out (e.g., the signal the optical sensors generate may be sampled, processed, and/or stored). The readout at this stage may serve several functions depending on the exact assay protocol and/or application. For example, the total number of particles 4 may be quantified and/or estimated prior to any separation steps so that this number may be stored in memory and used later in calculating a ratio of particles 4 removed or remaining in one or more optical sensing areas 41. Optical sensors 40 may be readout continuously and dynamics of sedimenting particles 4 (e.g., sedimentation velocity, binding rate kinetics, or combinations thereof) may be measured. Various statistical checks and/or error checks may be performed at this stage, such as a statistical analysis of particle distribution to detect any clumping and other non-idealities that may affect assay performance. The measurement of particles prior to separation step (i.e., STEP 230) is not necessary and STEP 226 may be omitted. After STEP 226, the process proceeds to STEP 228.

In STEP 228, binding force measurements may be performed on non-specifically bound particles 4 and/or specifically-bound magnetic particles. As described above, one or more regions on the chip may be used for binding force measurements where magnetic separation forces are continuously increased to determine when bonds break (i.e., when the particles are removed). Statistical analyses may be performed to extract the patterns and peaks in the separation rate of particles as to optimize the force intensity and/or duration to obtain the highest signal to noise ratio in the assay result. STEP 228 may occur before an assay starts and even may take place during a testing process after manufacturing. The binding forces may be stored in memory and may be used to adjust the magnetic separation field generators so that the highest signal to noise ratio is achieved between non-specifically bound and specifically bound magnetic particles. The measurement of binding forces and calibration of magnetic separation field generators is not necessary and STEP 228 may be omitted. After STEP 228, the process proceeds to STEP 230.

In STEP 230, non-specifically bound particles are removed from optical sensing areas 41. As discussed above, this may be performed by magnetic separation field generators and also by any other forces (e.g., hydrodynamic washing forces, flow forces, gravity, centripetal forces, and other forces strong enough to remove non-specifically bound magnetic particles but not specifically-bound magnetic particles). Optical sensors 40 may be read out during magnetic separation in order to monitor the magnetic separation dynamically (e.g., by measuring the motion of the magnetic particles 81). Particles detected in STEP 226 may be sufficient (e.g., when measuring binding kinetics) and thus removal of non-specifically bound particles may not be necessary (i.e., STEP 230 may be omitted). After STEP 230, the process proceeds to STEP 232.

In STEP 232, the optical sensors are read out again to measure the amount and/or surface concentration of specifically-bound particles. Additionally, negative control regions and positive control regions may be read out as well and the amount and/or ratio of specifically binding particles may in the control regions may be used to modify assay calibration parameters (e.g., the standard curve). Any of the steps 224 through 232 may occur in parallel (e.g., separation, readout, concentration may occur concurrently). Particles detected in STEP 226 may be sufficient for the assay (e.g., when measuring binding kinetics) and a subsequent readout may not be necessary (i.e., STEP 232 may be omitted). After STEP 212, the process proceeds to STEP 234.

In STEP 234, the concentration of the target analyte may be calculated. As discussed above, the calculation may be performed by comparing the amount and/or concentration of particles binding specifically to the surface to the standard curve and other assay calibration parameters to determine what the concentration of the target analyte is. The standard curve may be programmed onto the IC 12 during manufacturing and might not be altered at all. STEP 234 may take place right after STEP 226 for certain cases (e.g., when measuring binding kinetics of nanoparticles). After STEP 234, the process proceeds to STEP 236. When using one or multiple analytes, the system 10 may draw conclusions from the various target analyte concentrations and display these conclusions. For example, the system 10 may provide a negative/positive indicator (e.g., for an influenza test) or the system 10 may calculate an indicator that takes a weighted value of the various target analyte concentrations (e.g., a cardiac Troponin and CK-MB concentrations may be used to output a heart attack risk indicator). After STEP 234, the process proceeds to STEP 236.

In STEP 236, the target analyte concentration and/or conclusion may be displayed on a display 1 internal or external to the system 10 or may be transferred elsewhere (e.g., via a wireless link, via a USB interface, and any other electronic connection). Prior to sending, the data may be encrypted according to regulatory standards. After STEP 236, the process ends.

STEPS 212-236 may be performed for each target analyte that is detectable by the system 10, either sequentially or in parallel, or STEPS 212-236 may be performed on multiple analytes at the same time.

In the presence of a source of light, the particles 4 that remain in the optical sensing area 41 on the surface 7 of the integrated circuit 12 may cast a shadow 34 or otherwise modulate the light incident on said surface 7. One or more shadows 34 and/or other effects of light modulation can be detected by an array of optical sensors embedded in the integrated circuit 12. The signals from the optical sensors can be processed by circuitry embedded in the integrated circuit 12.

The target species can react with the surface 7 of the integrated circuit 12 before the magnetic particles 81 are attracted by magnetic concentration force or gravitational force. This reaction may cause at least a portion of the magnetic particles 81 that reach the surface 7 of the integrated circuit 12 to bind specifically to the integrated circuit 12.

The platform described herein can be used for applications including, but not limited to, diagnostics such as simplex assays, parallel or multiplexed assays, DNA microarray assays, glucose, cholesterol, metabolites, and small molecules detection; environmental assays such as for food contamination, and water and/or soil contamination; proteomics such as protein-protein binding force measurements, protein-protein binding resonant frequencies, protein kinetics research; genomics such as DNA methylation profile, and DNA force measurements; magnetic particle 4AFM such as low 1/f noise AFM, AFM with digitally controlled force and frequency, and multiplexed AFM; Magneic Particle Characterization such as exploration of magnetic properties of particles of different sizes and characteristics; Low Cost Bio-sensor Networks such as integrated and direct wireless transmission of assay results, and real-time outbreak and/or contamination monitoring; and any combinations thereof.

Variations of the systems, devices and methods have been shown and described herein by way of example only. Variations, changes, and substitutions can occur. For example, the methods can be performed with any one or more elements of the methods absent, and any one or more element of the devices can be omitted. Various alternatives and combinations of elements between the variations described herein may be employed. All publications, patents, and patent applications mentioned in this specification are herein incorporated by reference to the same extent as if each individual publication, patent, or patent application was specifically and individually indicated to be incorporated by reference.

I claim:

1. A device for detection of a target analyte in an aqueous sample comprising;
    an integrated circuit;
    a functionalized surface of the integrated circuit;
    a light source to illuminate the surface of the integrated circuit;
    magnetic particles that display paramagnetic behavior, wherein the magnetic particles are on the surface of the integrated circuit; and
    an optical sensor embedded in the integrated circuit;
    wherein the magnetic particles are bound strongly and/or specifically to the surface of the integrated circuit through a biochemical bond after one or more chemical reactions involving one or more target species in an aqueous sample; and
    wherein the bound magnetic particles cast shadows and reduce the amount of light incident on the optical sensor; and
    wherein the optical sensor is sized to detect one magnetic particle specifically bound to the surface of the integrated circuit.

2. The device of claim 1, wherein the particles are partially opaque.

3. The device of claim 1, further comprising an optical module, wherein the optical module comprises at least one of a reflector, a lens, an optical fiber, and a light pipe configured to direct light onto the surface.

4. The device of claim 1, further comprising capillaries placed above the surface, and wherein the capillaries are transparent.

5. The device of claim 1, further comprising an optically transparent thin layer of metal on the surface.

6. The device of claim 1, wherein at least one particle is near the surface in a landing approach within the range of at least one optical sensor to sample a light intensity at short intervals to detect the particle that is approaching and about to land on the surface.

7. The device of claim 1, wherein the optical sensor comprises a CMOS photodiode.

8. The device of claim 7, wherein the number of magnetic particles on the surface is detected before and after a magnetic separation of the magnetic particles.

9. The device of claim 1, further comprising a magnetic separation field generator embedded in the integrated circuit, and wherein a magnetic field generated by the magnetic separation field generator is sufficient to produce a magnetic separation force to remove non-specifically bound magnetic particles from an optical sensing area.

10. The device of claim 1, further comprising concentration conductors embedded in the integrated circuit, and wherein magnetic concentration forces produced by current passing through the concentration conductors are sufficient to attract the magnetic particles to the optical sensing areas.

11. The device of claim 1, wherein the optical sensor is smaller than the magnetic particles.

12. The device of claim 1, further comprising a light shield, and wherein the light shield surrounds the optical sensor to reduce the angles of acceptance of light of the optical sensor.

13. The device of claim 12, wherein the optical sensor is larger than one of the particles, and wherein the opening in the light shield is smaller than one of the particles such that the aperture is fully covered by one of the particles.

14. The device of claim 1, further comprising vias, and wherein the vias reduce stray light from shining on the optical sensor.

15. The device of claim 1, wherein the optical sensor is similar in size to the magnetic particles.

16. The device of claim 1, wherein an array of optical sensors are embedded in the integrated circuit.

17. A device for detection of a target analyte in an aqueous sample comprising;
    an integrated circuit having a surface comprising a coating, wherein the coating comprises biological and/or chemical molecules that react specifically with a target analyte;
    magnetic particles bound strongly and/or specifically to the surface after reacting with the target analyte;
    a sensor embedded in the integrated circuit to detect the one or more specifically bound particles; and
    a first separation conductor and a second separation conductor, wherein the first separation conductor is on the same side of the sensor from the second separation conductor, and wherein the first separation conductor is closer to the sensor than the second separation conductor is to the sensor, and wherein the first separation conductor is able to be turned on, and wherein the second separation conductor is able to be turned on after the first separation conductor is turned on.

* * * * *